(12) United States Patent
Brookings et al.

(10) Patent No.: US 10,980,814 B2
(45) Date of Patent: Apr. 20, 2021

(54) FUSED PENTACYCLIC IMIDAZOLE DERIVATIVES AS MODULATORS OF TNF ACTIVITY

(71) Applicants: UCB Biopharma SRL, Brussels (BE); SANOFI, Paris (FR)

(72) Inventors: Daniel Christopher Brookings, Slough (GB); Teresa De Haro Garcia, Slough (GB); Yann Foricher, Paris (FR); Helen Tracey Horsley, Slough (GB); Martin Clive Hutchings, Slough (GB); James Andrew Johnson, Slough (GB); Malcolm Maccoss, Seabrook Island, SC (US); Mengyang Xuan, Slough (GB); Zhaoning Zhu, Slough (GB)

(73) Assignees: UCB Biopharma SRL, Brussels (BE); Sanofi, Paris (FR)

( * ) Notice: Subject to any disclaimer, the term of this patent is extended or adjusted under 35 U.S.C. 154(b) by 0 days.

(21) Appl. No.: 16/497,217

(22) PCT Filed: Apr. 24, 2018

(86) PCT No.: PCT/EP2018/060489
§ 371 (c)(1),
(2) Date: Sep. 24, 2019

(87) PCT Pub. No.: WO2018/197503
PCT Pub. Date: Nov. 1, 2018

(65) Prior Publication Data
US 2020/0046723 A1 Feb. 13, 2020

(30) Foreign Application Priority Data
Apr. 25, 2017 (EP) .................................. 17168027

(51) Int. Cl.
*C07D 487/18* (2006.01)
*A61K 31/55* (2006.01)

(52) U.S. Cl.
CPC ............ *A61K 31/55* (2013.01); *C07D 487/18* (2013.01)

(58) Field of Classification Search
None
See application file for complete search history.

(56) References Cited

U.S. PATENT DOCUMENTS

2015/0152065 A1 6/2015 Brookings et al.

FOREIGN PATENT DOCUMENTS

| WO | 2013/186229 | 12/2013 |
| WO | 2015/086525 | 6/2015 |
| WO | 2016/050975 | 4/2016 |

OTHER PUBLICATIONS

Torres-Castiblanco et al. Biomédica 2018;38: pp. 17-26. (Year: 2018).*
Sun et al. J. Med. Chem. 63, 8146-8156. (Year: 2020).*
Tansey et al., "The TNF superfamily in 2009: new pathways, new indications, and new drugs", Drug Discovery Today, vol. 14, Nos. 23/24, pp. 1082-1088, Dec. 2009.
Carneiro et al., "Emerging Role for TNF-z in Erectile Dysfunction", J Sex Med 2010; 7:3823-2834.
Wu et al., "Do TNF Inhibitors Reduce the Risk of Myocardial Infarction in Psoriasis Patients?", JAMA, May 15, 2013, vol. 309, No. 19, pp. 2043-2044.
Hauwemeiren et al., "Safe TNF-based antitumor therapy following p55TNFR reduction in intestinal epithelium", The Journal of Clinical Investigation, vol. 123, No. 6, Jun. 2013, pp. 2590-2603.
Bradley, Jr., "TNF-midiated inflammatory disease," Journal of Pathology, 2008; 214: 149-160.
Richmond, Victoria, "Small Molecules as Anti-TNF Drugs", Current Medicinal Chemistry, 2015, 22, 2920-2942.
Tansey, Malu, et al., "The TNF superfamily in 2009: new pathways, new indications, and new drugs", Elsevier Drug discovery Today, vol. 00, No. 00—Oct. 2009 pp. 1-7.

* cited by examiner

Primary Examiner — Emily A Bernhardt
(74) Attorney, Agent, or Firm — McDonnell Boehnen Hulbert & Berghoff LLP

(57) ABSTRACT

Disclosed herein are compounds of formula (I)

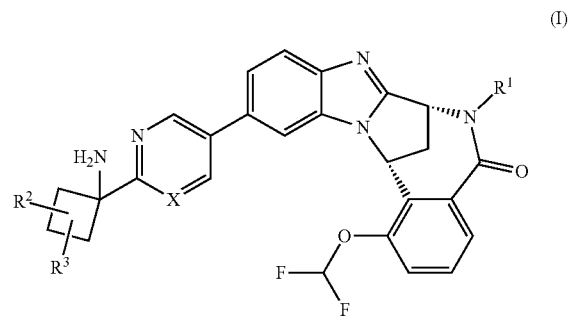

(I)

and pharmaceutically acceptable salt thereof, wherein variables X, $R^1$, $R^2$, and $R^3$ are defined herein. These compounds are potent modulators of human TNFα activity and, accordingly, of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

6 Claims, No Drawings

FUSED PENTACYCLIC IMIDAZOLE DERIVATIVES AS MODULATORS OF TNF ACTIVITY

This application is a U.S. national phase application of International Patent Application no. PCT/EP2018/060489 filed Apr. 24, 2018, which claims the benefit of European Patent Application no. 17168027.5 filed Apr. 25, 2017.

The present invention relates to a discrete class of fused pentacyclic imidazole derivatives, and to their use in therapy. More particularly, this invention is concerned with pharmacologically active substituted fused pentacyclic benzimidazole derivatives. These compounds act as modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition to their activity as potent modulators of human TNFα signalling, the compounds in accordance with the present invention also possess notable advantages in terms of their low liability to adverse cardiovascular side-effects (as demonstrated by weak activity in a standard hERG assay as described herein). Compounds of the invention also display low metabolic clearance, and a minimal propensity to induce drug-drug interactions (as demonstrated by weak inhibition of cytochrome P450 enzymes, including CYP3A4).

Furthermore, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2013/186229 relates to substituted benzimidazole derivatives which are modulators of the signalling of TNFα.

WO 2015/086525 relates to fused tricyclic imidazole derivatives which are modulators of the signalling of TNFα.

WO 2016/050975 relates to fused pentacyclic imidazole derivatives which are modulators of the signalling of TNFα.

The present invention provides a compound of formula (I), or a pharmaceutically acceptable salt thereof:

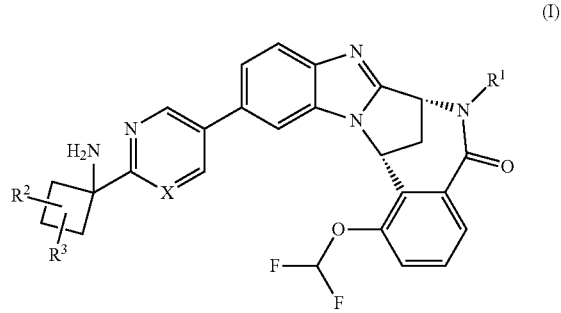

wherein
X represents N or C—F;
$R^1$ represents hydrogen or methyl;
$R^2$ represents hydrogen, methyl or trifluoromethyl; and
$R^3$ represents hydrogen, cyano, hydroxy or hydroxymethyl.

The compounds in accordance with the present invention are encompassed within the generic scope of WO 2016/050975. There is, however, no specific disclosure therein of a compound of formula (I) as defined above, or a pharmaceutically acceptable salt thereof.

The present invention also provides a compound of formula (I) as defined above, or a pharmaceutically acceptable salt thereof, for use in therapy.

The present invention also provides a compound of formula (I) as defined above, or a pharmaceutically acceptable salt thereof, for use in the treatment and/or prevention of disorders for which the administration of a modulator of TNFα function is indicated.

In another aspect, the present invention provides a compound of formula (I) as defined above, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above, or a pharmaceutically acceptable salt thereof.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium; D) or $^3$H (tritium; T) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

In a first embodiment, X represents N. In a second embodiment, X represents C—F.

In a first embodiment, $R^1$ represents hydrogen. In a second embodiment, $R^1$ represents methyl.

In a first embodiment, $R^2$ represents hydrogen. In a second embodiment, $R^2$ represents methyl. In a third embodiment, $R^2$ represents trifluoromethyl.

Suitably, $R^2$ represents hydrogen or methyl.

Suitably, $R^2$ represents hydrogen or trifluoromethyl.

In a first embodiment, $R^3$ represents hydrogen. In a second embodiment, $R^3$ represents cyano. In a third embodiment, $R^3$ represents hydroxy. In a fourth embodiment, $R^3$ represents hydroxymethyl (including —CD$_2$OH).

Suitably, $R^2$ and $R^3$ both represent hydrogen.

Suitably, $R^2$ represents methyl, and $R^3$ represents hydrogen.

Suitably, $R^2$ represents methyl, and $R^3$ represents cyano.

Suitably, $R^2$ represents methyl, and $R^3$ represents hydroxy.

Suitably, $R^2$ represents methyl, and $R^3$ represents hydroxymethyl (including —CD$_2$OH).

Suitably, $R^2$ represents trifluoromethyl, and $R^3$ represents hydroxy.

Particular sub-classes of compounds in accordance with the present invention include the compounds of formula (IIA) and (IIB), and pharmaceutically acceptable salts thereof:

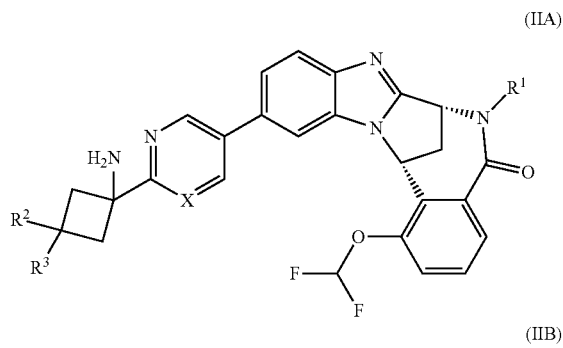

(IIA)

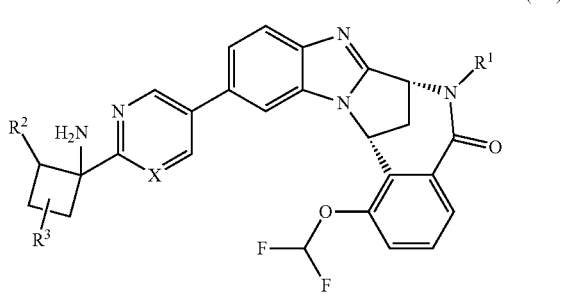

(IIB)

wherein X, $R^1$, $R^2$ and $R^3$ are as defined above.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behcet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound of formula (I) as defined above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a compound of formula (III) with a compound of formula (IV):

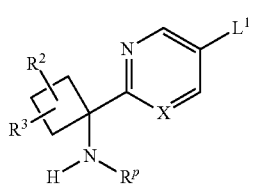
(III)

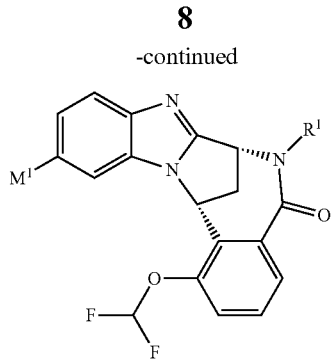
(IV)

wherein X, $R^1$, $R^2$ and $R^3$ are as defined above, $L^1$ represents a suitable leaving group, $M^1$ represents a boronic acid moiety —B(OH)$_2$ or a cyclic ester thereof formed with an organic diol, e.g. pinacol, 1,3-propane-diol or neopentyl glycol, and $R^P$ represents an N-protecting group; in the presence of a transition metal catalyst; followed, as necessary, by removal of the N-protecting group $R^P$.

The leaving group $L^1$ is typically a halogen atom, e.g. bromo.

The N-protecting group $R^P$ suitably represents tert-butoxycarbonyl (BOC). Alternatively, the N-protecting group $R^P$ may suitably represent tert-butylsulfinyl.

The transition metal catalyst of use in the reaction between compounds (III) and (IV) is suitably tris(dibenzylideneacetone)dipalladium(0), or [1,1'-bis(diphenylphosphino)-ferrocene]dichloropalladium(II), or chloro(2-dicyclohexylphosphino-2',4',6'-triisopropyl-1,1'-biphenyl)[2-(2'-amino-1,1'-biphenyl)]palladium(II) (XPhos Pd G2). The transition metal catalyst may typically be utilised in conjunction with 2-dicyclohexylphosphino-2',4',6'-triisopropyl-biphenyl (XPhos) or tricyclohexylphosphonium tetrafluoroborate. The reaction is suitably performed in the presence of potassium phosphate or potassium carbonate. The reaction is conveniently carried out at an elevated temperature in a suitable solvent, e.g. a cyclic ether such as 1,4-dioxane, optionally in admixture with water.

Where the N-protecting group $R^P$ is BOC or tert-butylsulfinyl, the subsequent removal thereof may conveniently be effected by treatment with an acid, e.g. a mineral acid such as hydrochloric acid, or an organic acid such as trifluoroacetic acid.

The intermediates of formula (IV) above wherein $M^1$ represents a cyclic ester of a boronic acid moiety —B(OH)$_2$ formed with pinacol may be prepared by reacting bis(pinacolato)diboron with a compound of formula (V):

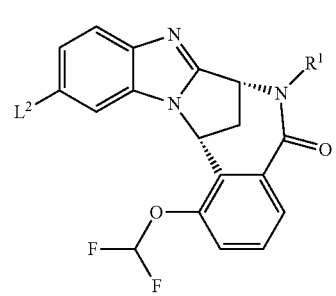
(V)

wherein $L^2$ represents a suitable leaving group; in the presence of a transition metal catalyst.

The leaving group $L^2$ is typically a halogen atom, e.g. chloro.

The transition metal catalyst of use in the reaction between bis(pinacolato)diboron and compound (V) is suitably tris(dibenzylideneacetone)dipalladium(0), which may be utilised in conjunction with 2-dicyclohexylphosphino-2',4',6'-triisopropylbiphenyl (XPhos) or tricyclohexylphosphonium tetrafluoroborate. The reaction is suitably performed in the presence of potassium acetate. The reaction is conveniently carried out at an elevated temperature in a suitable solvent, e.g. a cyclic ether such as 1,4-dioxane.

The intermediates of formula (V) above wherein $R^1$ is methyl may be prepared from the corresponding compound of formula (V) wherein $R^1$ is hydrogen by reaction with a methyl halide, e.g. iodomethane. The methylation reaction is generally performed in the presence of a base, e.g. a silylamide base such as potassium bis(trimethylsilyl)amide. The reaction may conveniently be carried out in a suitable solvent, e.g. a cyclic ether solvent such as tetrahydrofuran.

The intermediate of formula (V) above wherein $R^1$ is hydrogen and $L^2$ represents chloro is specifically disclosed in WO 2016/050975, as also is the intermediate of formula (IV) above wherein $R^1$ is hydrogen and $M^1$ represents 4,4,5,5-tetramethyl-1,3,2-dioxa-borolan-2-yl.

Where they are not commercially available, the starting materials of formula (III) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes give rise to mixtures of stereoisomers, these isomers may be separated by conventional techniques. In particular, where it is desired to obtain a particular enantiomer, this may be produced from a corresponding mixture of enantiomers using any suitable conventional procedure for resolving enantiomers. Thus, for example, diastereomeric derivatives, e.g. salts, may be produced by reaction of a mixture of enantiomers, e.g. a racemate, and an appropriate chiral compound, e.g. a chiral acid or base. The diastereomers may then be separated by any convenient means, for example by crystallisation, and the desired enantiomer recovered, e.g. by treatment with an acid in the instance where the diastereomer is a salt. In another resolution process a racemate may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used where it is desired to obtain a particular geometric isomer. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The compounds in accordance with the present invention potently neutralise the activity of TNFα in a commercially available HEK-293 derived reporter cell line known as HEK-Blue™ $CD_{40}L$. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 10 nM or better (the skilled person will appreciate that a lower $IC_{50}$ figure denotes a more active compound).

The compounds in accordance with the present invention display weak activity when tested in the standard hERG assay described herein (which is indicative of a liability to adverse cardiovascular side-effects). Indeed, when tested in that assay, compounds of the present invention exhibit an $IC_{50}$ value of at least 5 μM (the skilled person will appreciate that, in the hERG assay, a higher $IC_{50}$ figure denotes a superior compound, i.e. a compound less likely to be prone to adverse cardiovascular side-effects).

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 10 nM or better.

When tested in the reporter gene assay, the compounds of the accompanying Examples exhibit $IC_{50}$ values generally in the range of 0.01 nM to 10 nM.

hERG Assay

Pharmacological activity of the compounds at cardiac hERG channels (Kv11.1) was assessed functionally using an automated planar patch-clamp electrophysiology station. CHO cells stably expressing human hERG channels were grown under the permanent pressure of the appropriate selection antibiotics according to the specifications of the manufacturer (hERG-Duo cells, B'SYS GmbH, Switzerland). Cells were harvested below 80% confluence, suspended in serum-free medium and dispensed automatically to multi-well recording plates for whole-cell voltage-clamp recordings on a QPatch HTX workstation (Sophion, Biolin-Scientific AB, Denmark). The composition of the extracellular recording buffer was (in mM): NaCl, 150; KCl, 4; $CaCl_2$), 2; $MgCl_2$, 1; HEPES, 10; and glucose, 10; adjusted to pH 7.4 with NaOH. The intracellular buffer contained (in mM): KCl, 120; $CaCl_2$), 5; $MgCl_2$, 2; EGTA, 10; HEPES, 10; and Mg-ATP, 4; adjusted to pH 7.2 with KOH. The voltage protocol used to activate hERG currents consisted in a first depolarizing step from a −80 mV holding potential to +20 mV for 5 s followed by a second repolarizing step to −50 mV. Cycle time was 15 s, recordings were performed at room temperature and drug effects were evaluated on the peak tail-current elicited by the second repolarizing step. For pharmacology, stock solutions of the test articles at 10 mM were prepared in DMSO. A 6-point concentration-range was prepared in polypropylene micro-titer plates by first serially diluting the initial 10 mM stock 1:3 in DMSO and then diluting each of the 6 intermediate working solutions 1:333 in extracellular recording medium containing 0.06% Pluronic F-68 (Gibco/Thermofischer, France). Final concentrations of test articles (i.e. 0.12 µM, 0.37 µM, 1.1 µM, 3.3 µM, 10 µM and 30 µM) were applied cumulatively to the cells in ascending order. A positive control (terfenadine, 10 µM) was added at the end of each recording sequence. Time-course of hERG tail current amplitude was analyzed off-line following optional leak current substraction and compensation of current rundown as needed. Half-maximal inhibitory concentrations ($IC_{50}$) were obtained by fitting current amplitudes measured at the end of each exposure period and normalized with respect to pre-drug baseline with a four parameter sigmoidal equation.

When tested in the hERG assay, the compounds of the accompanying Examples were all found to exhibit an $IC_{50}$ value of at least 5 µM. Specifically, the compound of Example 6 exhibits an $IC_{50}$ value of approximately 8 µM; the compound of Example 9 exhibits an $IC_{50}$ value of approximately 20 µM; and the compounds of Examples 1-5, 7, 8 and 10-16 all exhibit an $IC_{50}$ value of >30 µM.

The following Examples illustrate the preparation of compounds according to the invention.

EXAMPLES

Abbreviations

DCM: dichloromethane EtOAc: ethyl acetate
MeOH: methanol THF: tetrahydrofuran
DMSO: dimethyl sulfoxide DMF: N,N-dimethylformamide
TBAF: tetra-n-butylammonium fluoride LDA: lithium diisopropylamide
Dess-Martin periodinane: 1,1,1-tris(acetyloxy)-1,1-dihydro-1,2-benziodoxol-3-(1H)-one
XPhos: 2-dicyclohexylphosphino-2',4',6'-triisopropylbiphenyl
XPhos Pd G2: chloro(2-dicyclohexylphosphino-2',4',6'-triisopropyl-1,1'-biphenyl)[2-(2'-amino-1,1'-biphenyl)]palladium(II)

| r.t.: room temperature | h: hour |
| M: mass | RT: retention time |

HPLC: High Performance Liquid Chromatography
LCMS: Liquid Chromatography Mass Spectrometry
ES+: Electrospray Positive Ionisation
Analytical Conditions All NMR spectra were obtained at 250 MHz, 300 MHz, 400 MHz or 500 MHz.

All reactions involving air- or moisture-sensitive reagents were performed under a nitrogen atmosphere using dried solvents and glassware.

LCMS Data Determination

Method 1

Column: X-Bridge C18 Waters 2.1×20 mm, 2.5 µm column

Mobile Phase A: 10 mM ammonium formate in water+0.1% ammonia solution

Mobile Phase B: acetonitrile+5% water+0.1% ammonia solution

Gradient program: Flow rate pump 1: 1 mL/min; Flow rate pump 2: 0.5 mL/min

| Pump 1: | | | Pump 2: | | |
| --- | --- | --- | --- | --- | --- |
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 2

Column: X-Bridge C18 Waters 2.1×20 mm, 2.5 µm column

Mobile Phase A: 10 mM ammonium formate in water+0.1% formic acid

Mobile Phase B: acetonitrile+5% water+0.1% formic acid

Gradient program: Flow rate pump 1: 1 mL/min; Flow rate pump 2: 0.5 mL/min

| Pump 1: | | | Pump 2: | | |
| --- | --- | --- | --- | --- | --- |
| Time | A % | B % | Time | A % | B % |
| 0.00 | 95.00 | 5.00 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.00 | 5.00 | | | |

Method 3

Column: X-Bridge C18 Waters 2.1×20 mm, 2.5 µm column

Mobile Phase A: 10 mM ammonium formate in water+0.1% ammonia solution

Mobile Phase B: acetonitrile+5% water+0.1% ammonia solution

Gradient program: Flow rate 1 mL/min

| Time | A % | B % |
| --- | --- | --- |
| 0.00 | 96.00 | 4.00 |
| 1.50 | 5.00 | 95.00 |
| 2.25 | 5.00 | 95.00 |
| 2.50 | 96.00 | 4.00 |

Method 4
Column: X-Bridge C18 Waters 2.1×20 mm, 2.5 µm column
Mobile Phase A: 10 mM ammonium formate in water+0.1% ammonia solution
Mobile Phase B: acetonitrile+5% water+0.1% ammonia solution
Gradient program: Flow rate 1 mL/min

| Time | A % | B % |
|---|---|---|
| 0.00 | 96.00 | 4.00 |
| 4.00 | 5.00 | 95.00 |
| 5.00 | 5.00 | 95.00 |
| 5.10 | 96.00 | 4.00 |

Method 5
Column: X-Bridge C18 Waters 2.1×20 mm, 2.5 µm column
Mobile Phase A: 10 mM ammonium formate in water+0.1% ammonia solution
Mobile Phase B: acetonitrile+5% water+0.1% ammonia solution
Gradient program: Flow rate 1 mL/min

| Time | A % | B % |
|---|---|---|
| 0.00 | 94.00 | 6.00 |
| 1.50 | 5.00 | 95.00 |
| 2.25 | 5.00 | 95.00 |
| 2.50 | 94.00 | 6.00 |

Method 6
Agilent Technologies 1260 Infinity

| Part | Model |
|---|---|
| LC/MSD | G6130B |
| Degasser | G4225A |
| BinPump | G1312B |
| HiP ALS (autosampler) | G1367E |
| Valve Drive | G1170A |
| TCC | G1316A |
| DAD VL | G1315D |
| Interface | 5900E |

Apparatus
Agilent 1260 Bin. Pump: G1312B, degasser; autosampler, ColCom. DAD: Agilent G1315D, 220-320 nm. MSD: Agilent LC/MSD G6130B ESI, pos/neg 100-800, ELSD Alltech 3300.
Gas flow: 1.5 mL/minute; Gas temp.: 40° C.; Column: Waters XSelect™ C18, 30×2.1 mm, 3.5 µm; Temperature: 35° C.; Flow: 1 mL/minute; Gradient: $t_0$=5% A, $t_{1.6\ min}$=98% A, $t_{3.0\ min}$=98% A; Post-time: 1.3 minutes; Eluent A: 0.1% formic acid in acetonitrile; Eluent B: 0.1% formic acid in water.

Method 7
Agilent Technologies 1260 Infinity

| Part | Model |
|---|---|
| LC/MSD | G6130B |
| Degasser | G4225A |
| BinPump | G1312B |
| HiP ALS (autosampler) | G1367E |
| Valve Drive | G1170A |
| TCC | G1316A |
| DAD VL | G1315D |
| Interface | 5900E |

Apparatus
Agilent 1260 Bin. Pump: G1312B, degasser; autosampler, ColCom. DAD: Agilent G1315D, 220-320 nm. MSD: Agilent LC/MSD G6130B ESI, pos/neg 100-800, ELSD Alltech 3300.
Gas flow 1.5 mL/minute; Gas temp.: 40° C.; Column: Waters XSelect™ C18, 50×2.1 mm, 3.5 µm; Temperature: 35° C.; Flow: 0.8 mL/minute; Gradient: $t_0$=5% A, $t_{3.5\ min}$=98% A, $t_{6.0\ min}$=98% A; Post-time: 2.0 minutes; Eluent A: 0.1% formic acid in acetonitrile; Eluent B: 0.1% formic acid in water.

Method 8
Column: Kinetex Core-Shell C18, 50×2.1 mm, 5 µm column protected by Phenomenex 'Security Guard' column
Mobile Phase A: 0.1% formic acid in water
Mobile Phase B: 0.1% formic acid in acetonitrile
Gradient program: Flow rate 1.2 mL/min
Column temperature: 40° C.

| Time | A % | B % |
|---|---|---|
| 0.00 | 95 | 5 |
| 1.20 | 0 | 100 |
| 1.30 | 0 | 100 |
| 1.31 | 95 | 5 |

Method 9
Column: Phenomenex Kinetex Core-Shell C8, 50×2.1 mm, 5 µm column protected by Phenomenex 'Security Guard' column
Mobile Phase A: 0.1% formic acid in water
Mobile Phase B: 0.1% formic acid in acetonitrile
Gradient program: Flow rate 1.2 mL/min
Column temperature: 40° C.

| Time | A % | B % |
|---|---|---|
| 0.00 | 95 | 5 |
| 1.83 | 0 | 100 |
| 2.25 | 0 | 100 |
| 2.26 | 95 | 5 |

Method 10
Column: Phenomenex Gemini C18, 2.0 mm×50 mm, 3 µm column
Mobile Phase A: 2 mM ammonium bicarbonate, pH 10
Mobile Phase B: acetonitrile
Gradient program: Flow rate 1.0 mL/minute
Column temperature: 60° C.

| Time | A % | B % |
|---|---|---|
| 0.00 | 99 | 1 |
| 1.80 | 0 | 100 |
| 2.10 | 0 | 100 |
| 2.30 | 99 | 1 |

Method 11
Mobile Phase A: 0.1% formic acid in water
Mobile Phase B: 0.1% formic acid in acetonitrile
Gradient program: Flow rate 0.6 mL/min
Column temperature: 40° C.

| Time | A % | B % |
|---|---|---|
| 0.00 | 95 | 0 |
| 5.30 | 0 | 100 |
| 5.80 | 0 | 100 |
| 5.82 | 95 | 5 |

GCMS Data Determination
Method 12
Agilent Technologies

| Part | Model |
|---|---|
| 5973 MSD | G2577A |
| autosampler | G2614A |
| 7683B injector | G2913A |
| 6890N GC system | G1530N |

Instrument: GC: Agilent 6890N, FID: Detection temp.: 300° C. and MS: 5973 MSD, EI-positive, Detection temp.: 280° C.; Mass range: 50-550; Column: RXi-5MS 20 m, ID 180 µm, df 0.18 µm; Average velocity: 50 cm/s; Injection vol.: 1 µL; Injector temp.: 250° C.; Split ratio: 20/1; Carrier gas: He; Initial temperature: 100° C.; Initial time: 1.5 minute; Solvent delay: 1.3 minute; Rate: 75° C./minute; Final temp.: 250° C.; Final time: 2.5 minutes.

Intermediate 1

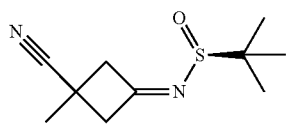

(R)—N-(3-Cyano-3-methylcyclobutylidene)-2-methylpropane-2-sulfinamide

To 1-methyl-3-oxocyclobutanecarbonitrile (532 mg, 4.63 mmol) dissolved in THF (35 mL) was added (R)-(+)-2-methyl-2-propanesulfinamide (570 mg, 4.61 mmol), followed by titanium(IV) ethoxide (1.8 mL, 8.7 mmol). The reaction mixture was heated at 75° C. under nitrogen overnight with stirring, then cooled to r.t. Saturated aqueous sodium bicarbonate solution (50 mL) was added. The reaction mixture was filtered through celite, washing with EtOAc. The organic layer was separated and washed sequentially with water (50 mL), followed by brine (50 mL). The organic layer was separated and filtered through a phase separator, then the organic layer was concentrated in vacuo. The resulting orange oil was purified by flash column chromatography on silica (gradient elution with 100% isohexane to 100% EtOAc). The resulting straw-coloured oil solidified on standing to afford the title compound (863 mg, 88%) as an off-white solid. $\delta_H$ (300 MHz, DMSO-$d_6$) 3.95-3.59 (m, 2H), 3.60-3.36 (m, 1H), 3.25 (ddt, J 17.6, 9.8, 3.3 Hz, 1H), 1.58 (d, J 1.4 Hz, 3H), 1.16 (d, J 1.2 Hz, 9H).

Intermediate 2

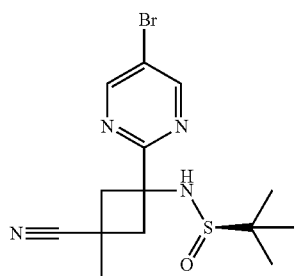 [SMILES: CC1(C#N)CC(N[S@](=O)C(C)(C)C)(c2ncc(Br)cn2)C1]

(R)—N-[1-(5-Bromopyrimidin-2-yl)-3-cyano-3-methylcyclobutyl]-2-methylpropane-2-sulfinamide Two separate batches of 5-bromo-2-iodopyrimidine (1.6 g, 5.62 mmol) were dissolved in DCM (50 mL) and DCM (100 mL). The separate reaction mixtures were cooled to −78° C. under nitrogen, then 2.5M n-butyllithium (2.26 mL, 5.65 mmol) was added to each reaction mixture dropwise over 5 minutes. The reaction mixtures were stirred at −78° C. under nitrogen for 2 minutes, prior to the slow addition of Intermediate 1 (1 g, 4.71 mmol) dissolved in DCM (5 mL) via syringe to each reaction mixture. The reaction mixtures were stirred at −78° C. for 2 h. The larger (100 mL) batch was stirred in an ice bath for 3 h, whilst the smaller (50 mL) batch was stirred in a cardice/acetone bath for 3 h. The reaction mixtures were combined and quenched with saturated aqueous ammonium chloride solution (50 mL), then the organic layer was separated, filtered through a phase separator and concentrated in vacuo. The resulting crude yellow oil was purified by flash column chromatography on silica (gradient elution with 100% isohexane to 100% EtOAc) to afford the title compound (530 mg, 14%) (60:40 mixture of trans:cis isomers) as a yellow gum. LCMS (ES+) [M+H]$^+$ 371.0, RT 1.66 and 1.69 minutes, purity 68.1% (Method 4).

Intermediate 3

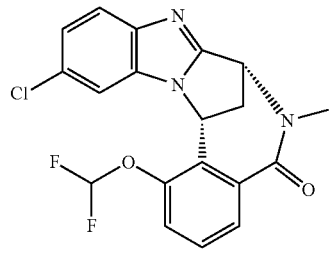 [SMILES: CN1C(=O)c2cccc(OC(F)F)c2[C@H]2C[C@@H]1c1nc3ccc(Cl)cc3n12]

(7R,14R)-11-Chloro-1-(difluoromethoxy)-6-methyl-6,7-dihydro-7,14-methanobenzimidazo[1,2-b][2,5]benzodiazocin-5(14H)-one To a solution of (7R,14R)-11-chloro-1-(difluoromethoxy)-6,7-dihydro-7,14-methanobenzimidazo[1,2-b][2,5]benzodiazocin-5(14H)-one (WO 2016/050975, Example 11) (10 g, 26.6 mmol) in dry THF (135 mL), cooled to −78° C. under nitrogen, was added potassium bis(trimethylsilyl)amide (1M in THF, 30 mL, 30 mmol) dropwise over 15 minutes. The resulting mixture was stirred at −78° C. for 1 h prior to the addition of iodomethane (2.5 mL, 40 mmol) dropwise over 5 minutes. The reaction mixture was stirred at −78° C. for 1 h, then allowed to warm slowly to ambient temperature overnight. The reaction mixture was poured into saturated aqueous ammonium chloride solution (600 mL) and extracted with EtOAc (2×800 mL). The organic extracts were dried (Na$_2$SO$_4$), filtered and concentrated in vacuo. Purification by flash chromatography on silica (elution with 5% MeOH/DCM) afforded the title compound (9.12 g, 88%) as a beige solid. δ$_H$ (300 MHz, DMSO-d$_6$) 8.33-8.21 (m, 1H), 7.87-7.33 (m, 5H), 7.22 (dd, J 8.7, 2.1 Hz, 1H), 6.23 (d, J 7.1 Hz, 1H), 5.22 (d, J 7.1 Hz, 1H), 3.55-3.41 (m, 1H), 3.33 (s, 3H), 2.81 (d, J 13.8 Hz, 1H). LCMS (ES+) [M+H]$^+$ 390.0, RT 1.10 minutes (Method 3).

Intermediate 4

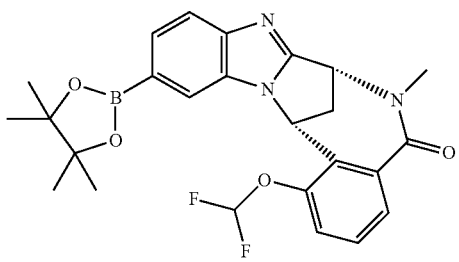 [SMILES: CN1C(=O)c2cccc(OC(F)F)c2[C@H]2C[C@@H]1c1nc3ccc(B4OC(C)(C)C(C)(C)O4)cc3n12]

(7R,14R)-1-(Difluoromethoxy)-6-methyl-11-(4,4,5,5-tetramethyl-1,3,2-dioxaborolan-2-yl)-6,7-dihydro-7,14-methanobenzimidazo[1,2-b][2,5]benzodiazocin-5(14H)-one Intermediate 3 (4 g, 10.3 mmol) in 1,4-dioxane (42 mL) was treated with bis-(pinacolato)diboron (3.9 g, 15 mmol) and potassium acetate (3 g, 30.6 mmol). The reaction mixture was degassed and flushed with nitrogen. Tris(dibenzylideneacetone)-dipalladium(0) (484 mg, 0.51 mmol) and tricyclohexylphosphonium tetrafluoroborate (390 mg, 1.03 mmol) were added, then the reaction mixture was degassed and flushed with nitrogen, before being heated overnight at 140° C. Further bis(pinacolato)diboron (2.6 g, 10.3 mmol) was added. The reaction mixture was heated at 140° C. for 24 h, then partitioned between EtOAc and brine. The organic phase was separated and concentrated in vacuo, then purified by flash column chromatography on silica (gradient elution with 0-10% EtOAc/MeOH), to afford the title compound (2.5 g, 50%) as a white solid. LCMS (ES+) [M+H]$^+$ 482.2, RT 2.40 minutes (Method 4).

Intermediate 5

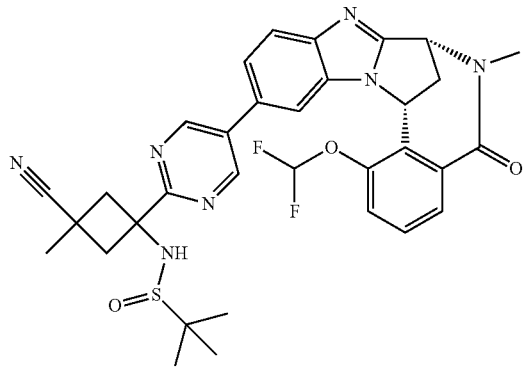 [SMILES: CN1C(=O)c2cccc(OC(F)F)c2[C@H]2C[C@@H]1c1nc3ccc(-c4cnc(C5(NS(=O)C(C)(C)C)CC(C)(C#N)C5)nc4)cc3n12]

(R)—N-(3-Cyano-1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}-3-methylcyclobutyl)-2-methylpropane-2-sulfinamide To potassium phosphate tribasic (171 mg, 0.80 mmol), tricyclohexylphosphonium tetrafluoroborate (18.8 mg, 0.050 mmol), tris(dibenzylideneacetone)dipalladium(0) (16.7 mg, 0.018 mmol) and Intermediate 4 (126 mg, 0.263 mmol) was added Intermediate 2 (83 mg, 0.225 mmol) dissolved in degassed 1,4-dioxane (1.5 mL). Degassed water (0.04 mL) was added and the reaction mixture was degassed under three cycles of vacuum and nitrogen, then transferred to a sealed tube and placed in a pre-heated block at 110° C. for 3 h. The reaction mixture was allowed to cool to ambient temperature, then diluted with EtOAc (20 mL) and water (20 mL). The organic layer was separated and the aqueous layer was extracted with additional EtOAc (20 mL). The organic layers were combined and washed with brine (20 mL), then dried (Na$_2$SO$_4$) and filtered. The solvent was removed in vacuo. The resulting brown oil was purified by flash column chromatography on silica (gradient elution with 100% isohexane to 100% EtOAc, followed by 100% DCM to 25% MeOH/DCM) to afford the title compound (178 mg, 92%) (mixture of trans and cis isomers) as a brown oil. LCMS (ES+) [M+H]$^+$ 646.2, RT 1.11 minutes (Method 3).

Intermediate 6

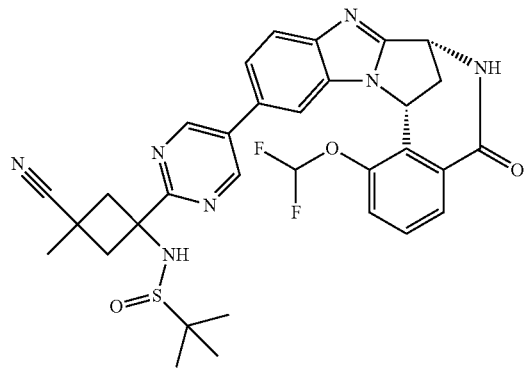 [SMILES: CC1(C#N)CC(NS(=O)C(C)(C)C)(c2ncc(-c3ccc4nc5n(c4c3)[C@@H]3C[C@H]5NC(=O)c4cccc(OC(F)F)c43)cn2)C1]

(R)—N-(3-Cyano-1-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-methylcyclobutyl)-2-methylpropane-2-sulfinamide To a mixture of potassium phosphate tribasic (80 mg, 0.377 mmol), Intermediate 2 (50 mg, 0.121 mmol) and (7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14M-one (WO 2016/050975, Intermediate 171) (60 mg, 0.128 mmol) under nitrogen were added tricyclohexylphosphonium tetrafluoroborate (5 mg, 0.013 mmol) and tris-(dibenzylideneacetone)dipalladium(0) (6 mg, 0.0064 mmol). The reagents were dissolved in 1,4-dioxane (3 mL) and water (0.2 mL) was added, then the reaction mixture was degassed under vacuum and nitrogen, before being heated at reflux overnight. The reaction mixture was diluted with EtOAc (20 mL)

and water (20 mL). The organic layer was separated and the aqueous layer was extracted with further EtOAc (20 mL). The organic layer was separated and filtered through a phase separator, then concentrated in vacuo. The resulting crude brown oil was purified by flash column chromatography on silica (gradient elution with 0-100% DCM/EtOAc, followed by 1-10% MeOH/EtOAc) to afford the title compound (51 mg, 57%) as a yellow solid. LCMS (ES+) [M+H]+ 632.0, RT 1.85 minutes (Method 1). LCMS (ES+) [M+H]+ 632.1, RT 1.81 minutes (Method 2).

Intermediate 7

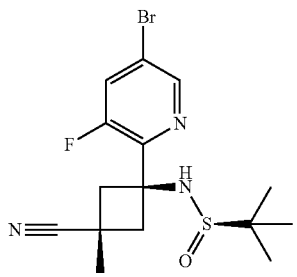 [SMILES: CC(C)(C)[S@@](=O)N[C@]1(c2ncc(Br)cc2F)C[C@@](C)(C#N)C1]

(R)—N-[trans-1-(5-Bromo-3-fluoropyridin-2-yl)-3-cyano-3-methylcyclobutyl]-2-methyl-propane-2-sulfinamide 2,5-Dibromo-3-fluoropyridine (536 mg, 2.11 mmol) was dissolved in DCM (100 mL) and cooled under nitrogen to −78° C. n-Butyllithium (2.5M, 0.9 mL, 2 mmol) was added dropwise, and the reaction mixture was stirred at −78° C. under nitrogen for 5 minutes, prior to the slow addition of Intermediate 1 (390 mg, 1.84 mmol) dissolved in DCM (10 mL) via syringe. The reaction mixture was stirred at −78° C. for 1 h, then for 2 h in an ice bath. The reaction mixture was quenched with saturated aqueous ammonium chloride solution (50 mL), then the organic layer was separated and washed with brine (50 mL). The organic layer was separated and filtered through a phase separator, then the solvent was removed in vacuo. The resulting crude dark red/brown oil was purified by flash column chromatography on silica (gradient elution with 100% isohexane to 100% EtOAc) to afford the title compound (220 mg, 28%). LCMS (ES+) [M+H]+ 388.0/390.0, RT 0.961 minutes (Method 3).

Intermediate 8

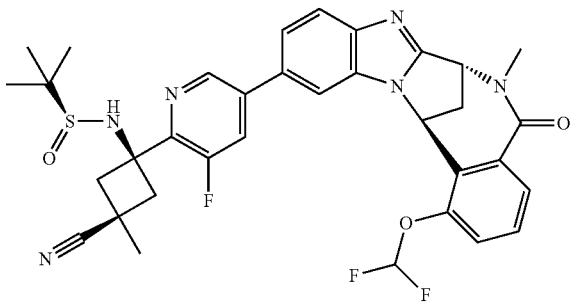 [SMILES: CN1C(=O)c2cccc(OC(F)F)c2[C@@H]2C[C@@H]1c1nc3ccc(-c4cnc([C@]5(N[S@@](=O)C(C)(C)C)C[C@@](C)(C#N)C5)c(F)c4)cc3n12]

(R)—N-(cis-3-Cyano-1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-3-methylcyclobutyl)-2-methylpropane-2-sulfinamide To a mixture of Intermediate 4 (113 mg, 0.241 mmol) and potassium phosphate tribasic (167 mg, 0.773 mmol) was added a solution of Intermediate 7 (75 mg, 0.193 mmol) in 1,4-dioxane (3 mL). The reaction mixture was degassed and flushed with nitrogen. Tris(dibenzylideneacetone)dipalladium(0) (9.1 mg, 0.0097 mmol) and tricyclohexylphosphonium tetrafluoroborate (8.8 mg, 0.023 mmol) in 1,4-dioxane were added with several drops of water. The reaction mixture was heated under microwave irradiation for 4 h at 120° C., then separated between EtOAc and brine. The organic layer was filtered through a phase separator and the organic phase was concentrated in vacuo. The crude residue was purified by flash column chromatography on silica (gradient elution with 100% isohexane to 100% EtOAc, followed by 1-15% MeOH/DCM) to afford the title compound (102 mg, 81%) as an off-white solid. LCMS (ES+) [M+H]+ 663, RT 1.32 minutes (Method 5).

Intermediate 9

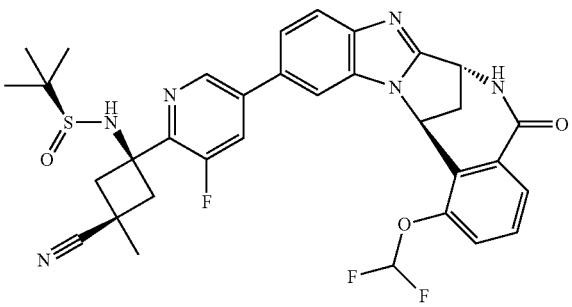 [SMILES: CC(C)(C)[S@](=O)N[C@]1(c2ncc(-c3ccc4nc5n(c4c3)[C@H]3C[C@H]5NC(=O)c4cccc(OC(F)F)c43)cc2F)C[C@](C)(C#N)C1]

(R)—N-(cis-3-Cyano-1-{5-[(7R,14R)-1-(difluoromethoxy)-5-oxo-5,6,7,14-tetrahydro-7,14-methanobenzimidazo[1,2-b][2,5]benzodiazocin-11-yl]-3-fluoropyridin-2-yl}-3-methylcyclobutyl)-2-methylpropane-2-sulfinamide (7R,14R)-1-(Difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (WO 2016/050975, Intermediate 171) (297 mg, 0.636 mmol) was treated with potassium phosphate tribasic (441 mg, 2.04 mmol), then Intermediate 7 (220 mg, 0.510 mmol) was added, followed by 1,4-dioxane (3 mL). The reaction mixture was degassed and flushed with nitrogen. Tris(dibenzylideneacetone)dipalladium(0) (24 mg, 0.025 mmol) and tricyclohexylphosphonium tetrafluoroborate (23 mg, 0.061 mmol) were added, together with several drops of water. The mixture was heated under microwave irradiation at 120° C. for 4 h. EtOAc and brine were added to the reaction mixture, which was stirred before filtration through a phase separator. The organic phase was concentrated in vacuo. The crude residue was purified by flash column chromatography on silica (gradient elution 100% isohexane to 100% EtOAc, followed by 1-15% MeOH in DCM) to afford the title compound (189 mg, 54%) as an off-white solid. LCMS (ES+) [M+H]+ 649.2, RT 1.32 minutes (Method 5).

Intermediate 10

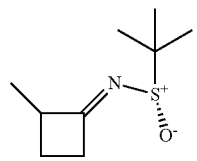

(S)-2-Methyl-N-(2-methylcyclobutylidene)propane-2-sulfinamide 2-Methylcyclobutan-1-one (1.00 g, 11.3 mmol) was dissolved in THF (30 mL) and (S)-2-methyl-2-propane-sulfinamide (1.20 g, 9.60 mmol) was added, followed by titanium(IV) ethoxide (4.0 mL, 19 mmol). The reaction mixture was stirred at r.t. for 48 h. Water (5 mL) was added and the mixture was stirred, then EtOAc (100 mL) was added, followed by Na₂SO₄ (10 g). After 15 minutes the mixture was filtered, and the solids were washed with EtOAc (3×15 mL). The combined organic layers were concentrated in vacuo. The crude residue was purified by flash column chromatography on silica (gradient elution with 0-40% EtOAc in isohexane) to afford the title compound (1.55 g, 86%) as a colourless oil. LCMS (ES+) [M+H]+ 188.2, RT 1.37 minutes and 1.41 minutes (Method 4).

Intermediate 11

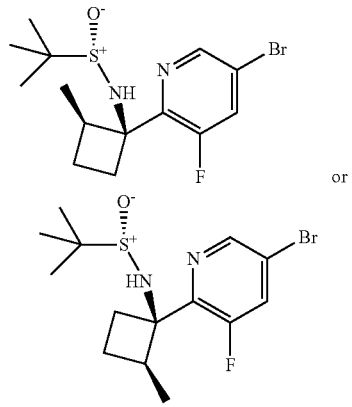

N-[(1S,2R)-1-(5-Bromo-3-fluoropyridin-2-yl)-2-methylcyclobutyl]-2-methylpropane-2-sulfinamide or N-[(1R,2S)-1-(5-Bromo-3-fluoropyridin-2-yl)-2-methylcyclobutyl]-2-methylpropane-2-sulfinamide 2,5-Dibromo-3-fluoropyridine (2.34 g, 8.81 mmol) was dissolved in DCM (30 mL) and cooled to −78° C. under nitrogen, then N-butyllithium (2.5M, 3.5 mL, 8.8 mmol) was added. The reaction mixture was stirred for 10 minutes prior to the addition of a solution of Intermediate 10 (1.50 g, 8.01 mmol) in DCM (3 mL). The mixture was stirred at −78° C. for 2 h, then quenched with saturated aqueous ammonium chloride solution (30 mL) and stirred for 5 minutes. The organic layer was separated and dried (Na₂SO₄), then filtered and concentrated in vacuo. The resulting crude residue was purified by flash column chromatography on silica (gradient elution with 0-45% EtOAc in isohexanes) to afford the title compound (800 mg, 27%; cis-isomer), plus a 3:1 mixture of predominantly trans-isomer with the other cis-isomer (650 mg, 22%).

Title compound: δ$_H$ (300 MHz, CDCl₃) 8.49-8.39 (m, 1H), 7.54 (dd, J 9.9, 1.9 Hz, 1H), 3.87 (s, 1H), 2.92 (dtt, J12.3, 9.0, 1.6 Hz, 1H), 2.71 (h, J7.4 Hz, 1H), 2.45-2.32 (m, 1H), 2.11-1.97 (m, 1H), 1.86-1.69 (m, 1H), 1.28-1.23 (m, 12H). LCMS (ES+) [M+H]+ 363.0 and 365.0, RT 2.28 minutes (Method 4).

Intermediate 12

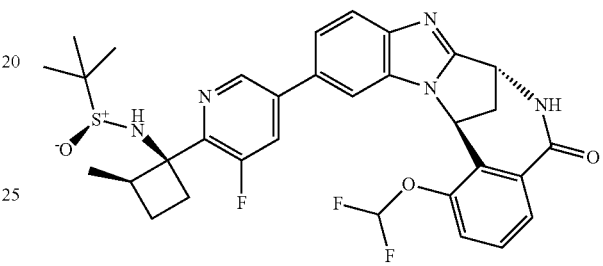

or

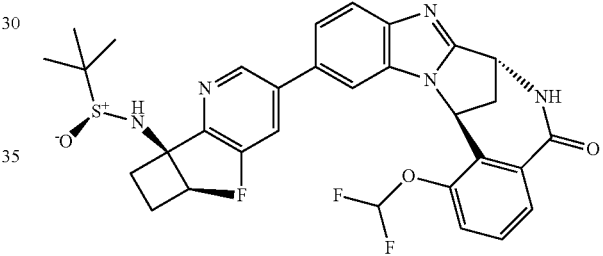

N-[(1S,2R)-1-{5-[(7R,14R)-1-(Difluoromethoxy)-5-oxo-5,6,7,14-tetrahydro-7,14-methanobenzimidazo[1,2-b][2,5]benzodiazocin-11-yl]-3-fluoropyridin-2-yl}-2-methylcyclobutyl]-2-methylpropane-2-sulfinamide or N-[(1R,2S)-1-{5-[(7R,14R)-1-(Difluoromethoxy)-5-oxo-5,6,7,14-tetrahydro-7,14-methanobenzimidazo[1,2-b][2,5]-benzodiazocin-11-yl]-3-fluoropyridin-2-yl}-2-methylcyclobutyl]-2-methylpropane-2-sulfinamide To Intermediate 11 (187 mg, 0.51 mmol), (7R,14R)-1-(difluoromethoxy)-11-(4,4,5,5-tetramethyl-1,3,2-dioxa-borolan-2-yl)-6,7-dihydro-7,14-methanobenzimidazo[1,2-b][2,5]benzodiazocin-5(14H)-one (WO 2016/050975, Intermediate 171) (200 mg, 0.43 mmol), tricyclohexylphosphonium tetrafluoroborate (16 mg, 0.042 mmol) and tris-(dibenzylideneacetone)dipalladium(0) (20 mg, 0.021 mmol) in 1,4-dioxane (5 mL) under nitrogen was added potassium phosphate tribasic (278 mg, 1.28 mmol) in water (1 mL). The reaction mixture was degassed under nitrogen, then sealed in a pressure tube and heated at 105° C. for 3 h. The reaction mixture was cooled to r.t., then partitioned between DCM and water. The organic layer was separated and dried (Na₂SO₄), then filtered and concentrated in vacuo. The crude residue was purified by flash column chromatography on silica (gradient elution 0-10% MeOH in DCM) to afford the title compound (145 mg, 54%) as a yellow solid. LCMS (ES+) [M+H]+ 624.2, RT 2.44 minutes (Method 4).

Intermediate 13

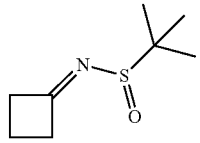

N-(Cyclobutylidene)-2-methylpropane-2-sulfinamide

A solution of cyclobutanone (100 g, 1.43 mol) in THF (722 mL) was cooled to 15-20° C. 2-Methyl-2-propanesulfinamide (144 g, 1.19 mol), cooled to 15-20° C., was added, followed by titanium(IV) isopropoxide (847 g, 2.98 mol). The reaction mixture was heated at 60° C. for 16 h, then concentrated in vacuo. The crude residue was purified by flash column chromatography on silica (gradient elution, 0-20% EtOAc/petroleum ether) to afford the title compound (combined yield from 19 batches: 2.14 kg, 55%) as a yellow oil. $\delta_H$ (400 MHz, DMSO-$d_6$) 3.37-3.17 (m, 1H), 3.14-3.07 (m, 3H), 2.06-1.99 (m, 2H), 1.14 (s, 9H).

Intermediate 14

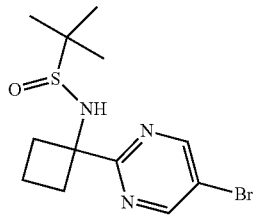 [SMILES: CC(C)(C)S(=O)NC1(c2ncc(Br)cn2)CCC1]

N-[1-(5-Bromopyrimidin-2-yl)cyclobutyl]-2-methylpropane-2-sulfinamide

5-Bromo-2-iodopyrimidine (345 g, 1.21 mol) was cooled to 15-20° C. and dissolved in anhydrous DCM (6 L). The reaction mixture was cooled to between −60° C. and −70° C., whereupon 2.5M n-butyllithium (450 mL, 1.13 mol) was added dropwise. The reaction mixture was stirred for 2 h at a temperature between −60° C. and −70° C., then a solution of Intermediate 13 (150 g, 866 mmol) in anhydrous DCM (150 mL) was added. The temperature was maintained between −60° C. and −70° C. for 2 h with stirring, before warming to 15-20° C. The reaction mixture was stirred for a further 12 h, then quenched with water (100 mL). Eleven batches were combined and extracted with DCM (2×3330 mL). The organic layer was washed with brine (1650 mL), separated and dried (Na$_2$SO$_4$), then filtered and concentrated in vacuo. The crude residue was purified by flash column chromatography on silica (gradient elution with 1:0:10 to 1:1:3 EtOAc/DCM/petroleum ether) to afford the title compound (combined yield from 11 batches: 1.38 kg, 44%) as a yellow solid. $\delta_H$ (400 MHz, DMSO-$d_6$) 9.00 (s, 2H), 2.65-2.45 (m, 2H), 2.44-2.42 (m, 2H), 1.99-1.94 (m, 1H), 1.73-1.70 (m, 1H), 1.07 (s, 9H).

Intermediate 15

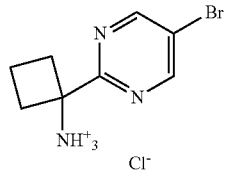

1-(5-Bromopyrimidin-2-yl)cyclobutanamine hydrochloride

In six separate batches Intermediate 14 (302 g, 909 mmol) was dissolved in MeOH (1.2 L) at 15-20° C. To the mixture was added MeOH/hydrochloric acid (600 mL), and the reaction mixture was stirred at 15-20° C. for 2 h. The six batches were combined and concentrated. To the crude residue were added isopropyl ether (9 L) and MeOH (1 L). The mixture was stirred for 1 h at 15-20° C. The solid was filtered, rinsed with DCM (3 L) and dried, to afford the title compound (1.21 kg, 84%) as a yellow solid. $\delta_H$ (400 MHz, CD$_3$OD) 9.02 (s, 2H), 2.84-2.82 (m, 2H), 2.81-2.78 (m, 2H), 2.60-2.27 (m, 2H).

Intermediate 16

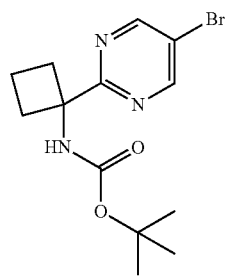 [SMILES: CC(C)(C)OC(=O)NC1(c2ncc(Br)cn2)CCC1]

tert-Butyl N-[1-(5-bromopyrimidin-2-yl)cyclobutyl]carbamate

To a suspension of Intermediate 15 (202 g, 764 mmol) in THF (400 mL), cooled on an ice bath, were added di-tert-butyl dicarbonate (183 g, 832 mmol) and triethylamine (154 g, 212 mL, 1.51 mol). The mixture was stirred at 0-5° C. for 30 minutes, then the ice bath was removed and the reaction mixture was allowed to reach ambient temperature. The reaction mixture was partitioned between EtOAc (1000 mL) and water (600 mL). The aqueous phase was separated, then the organic phase was washed sequentially with water (600 mL) and brine (2×200 mL). The organic phase was dried (Na$_2$SO$_4$), filtered and concentrated in vacuo. The resulting crude solid was dried overnight in vacuo at 50° C. to afford the title compound (254 g, quantitative) as an off-white solid. LCMS (ES+) [M+Na]+350.0, RT 2.20 minutes (Method 4).

Intermediate 17

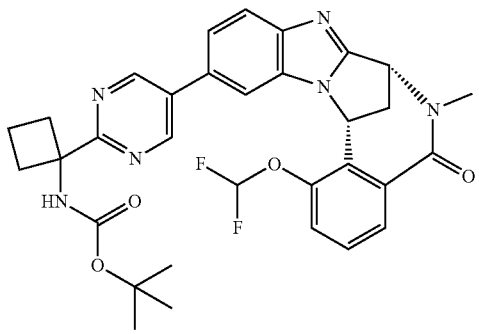 [SMILES: CN1C(=O)c2cccc(OC(F)F)c2[C@H]2C[C@@H]1c1nc3ccc(-c4cnc(C5(NC(=O)OC(C)(C)C)CCC5)nc4)cc3n12]

tert-Butyl (1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}cyclobutyl)-carbamate A flame-dried flask under nitrogen equipped with a reflux condenser was charged with Intermediate 3 (13.3 g, 34.0 mmol), tris(dibenzylideneacetone)dipalladium(0) (1.61 g, 1.71 mmol), XPhos (1.63 g, 3.43 mmol), bis(pinacolato)diboron (9.85 g, 38.8 mmol) and potassium acetate (8.5 g, 87 mmol), then 1,4-dioxane (136 mL) was added. The resulting mixture was stirred at 100° C. for 22 h before Intermediate 16 (12.3 g, 37.4 mmol) and aqueous tribasic potassium phosphate solution (1.27 mol/L, 40 mL, 50.8 mmol) were added. The reaction mixture was heated under reflux for 3 h before being charged with additional tris(dibenzylideneacetone)dipalladium(0) (500 mg, 0.53 mmol), XPhos (510 mg, 1.07 mmol) and aqueous tribasic potassium phosphate solution (1.27 mol/L, 20 mL, 25.4 mmol). The mixture was stirred for 1 h, then cooled to room temperature, diluted with DCM (600 mL) and washed with brine (400 mL). The aqueous phase was extracted with DCM (500 mL), then the combined organic extracts were passed through a phase separator and concentrated in vacuo. Purification by flash chromatography on silica (elution with 0-5% MeOH/DCM) afforded the title compound (18.0 g, 88%) as an off-white solid. $\delta_H$ (400 MHz, CDCl$_3$) 8.93 (s, 2H), 8.49 (dd, J8.2, 1.3 Hz, 1H), 7.84 (dd, J8.5, 0.7 Hz, 1H), 7.74-7.63 (m, 1H), 7.48-7.38 (m, 2H), 7.34-7.29 (m, 1H), 6.84 (t, J72.8 Hz, 1H), 6.31 (d, J7.2 Hz, 1H), 5.92 (s, 1H), 5.01 (d, J7.1 Hz, 1H), 3.53 (s, 3H), 3.51-3.43 (m, 1H), 2.90 (d, J 13.6 Hz, 1H), 2.84-2.57 (m, 3H), 2.22-2.07 (m, 3H), 1.43 (s, 9H). LCMS (ES+) [M+H]$^+$ 603.2, RT 1.25 minutes (Method 3).

Intermediate 18

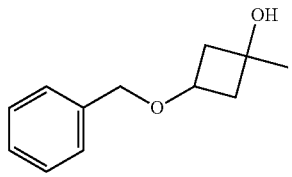

3-Benzyloxy-1-methylcyclobutanol

Methylmagnesium iodide was prepared by slow addition of iodomethane (42.6 mL, 681 mmol) to a mixture of magnesium (20.7 g, 851 mmol) in diethyl ether (500 mL). The mixture was heated on a warm water bath for 30 minutes. The solution of methylmagnesium iodide was cooled in a dry ice/acetone bath to an internal temperature of −25° C., then a solution of 3-benzyloxycyclobutan-1-one (94 mL, 567 mmol) in diethyl ether (100 mL) was added slowly, maintaining the internal temperature below −10° C. After the addition was complete, the mixture was stirred at −10° C., warming to 15° C. over 30 minutes. The reaction mixture was cooled to 0° C., then diluted with diethyl ether and quenched with saturated aqueous ammonium chloride solution. The organic layer was separated and the aqueous layer was extracted with diethyl ether (2×300 mL). The combined organic layers were filtered and washed with saturated aqueous ammonium chloride solution, then dried (Na$_2$SO$_4$), filtered and concentrated in vacuo, to afford the title compound (109 g, 100%) (~3:1 mixture of stereoisomers) as a yellow oil. GCMS: major isomer RT 3.664 (74.6%), [M-C$_7$H$_7$]$^+$101, [M-C$_5$H$_9$O$_2$]$^+$91; minor isomer RT 3.630 (25.4%), [M-C$_7$H$_7$]$^+$101, [M-C$_5$H$_9$O$_2$]$^+$91 (Method 12).

Intermediate 19

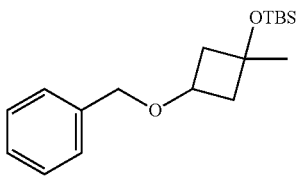 [SMILES: CC1(O[Si](C)(C)C(C)(C)C)CC(OCc2ccccc2)C1]

(3-Benzyloxy-1-methylcyclobutoxy)-tert-butyl(dimethyl)silane

Imidazole (190 g, 2.79 mol) was added to a solution of Intermediate 18 (107 g, 558 mmol) in DMF (1 L). tert-Butyl (chloro)dimethylsilane (252 g, 1.67 mmol) was added. The reaction mixture was stirred at r.t. overnight, then poured into ice-water. The aqueous phase was extracted with diethyl ether (3×500 mL). The organic layers were combined and washed with water, then dried (Na$_2$SO$_4$), filtered and concentrated in vacuo. The resulting crude yellow oil (291 g) was purified by flash column chromatography on silica (heptane, followed by 2% EtOAc in heptane) to afford the title compound (121 g, 46%) (~3:1 mixture of stereoisomers). Major isomer: $\delta_H$ (400 MHz, CDCl$_3$) 7.38-7.24 (m, 5H), 4.40 (s, 2H), 3.70-3.62 (m, 1H), 2.41-2.33 (m, 2H), 2.18-2.09 (m, 2H), 1.28 (s, 3H), 0.87 (s, 9H), 0.07 (s, 6H).

Intermediate 20

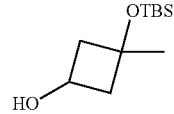

3-[tert-Butyl(dimethyl)silyl]oxy-3-methylcyclobutanol

A mixture of Intermediate 19 (121 g, 257 mmol) in ethanol (500 mL) was treated with Norit (or activated charcoal) (13 g) and stirred for 1 h. The mixture was filtered over kieselguhr and rinsed with ethanol (500 mL). The filtrate was transferred to a 3-neck round-bottomed flask (4 L) and the mixture was evacuated and back-filled three times with argon. A slurry of palladium on activated carbon (10%, 6.1 g, 5.73 mmol) in water was added and the mixture was evacuated and back-filled with argon. The mixture was evacuated and back-filled three times with hydrogen, then stirred overnight at r.t. The mixture was filtered through kieselguhr under a nitrogen flow, then rinsed with ethanol. The filtrate was concentrated in vacuo. The crude residue (68 g) was combined with additional batches (62 g and 63 g), then purified by flash column chromatography on silica (gradient elution with 10-20% EtOAc in heptane), to afford the title compound (164 g, 85%) (~8:2 mixture of isomers) as a colourless oil. $\delta_H$ (400 MHz, CDCl$_3$) 4.52-4.43 (m, 0.2H), 3.98-3.87 (m, 0.8H), 2.50-2.40 (m, 2H), 2.10-2.02 (m, 1.6H), 1.98-1.91 (m, 0.4H), 1.64-1.58 (m, 0.8H), 1.58-1.52 (m, 0.2H), 1.44 (s, 0.6H), 1.28 (s, 2.4H), 0.88 (s, 7H), 0.87 (s, 2H), 0.07 (s, 6H).

Intermediate 21

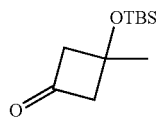

3-[tert-Butyl(dimethyl)silyl]oxy-3-methylcyclobutanone

To a solution of Intermediate 20 (192 g, 887 mmol) in DCM (2 L) at 5° C. was added Dess-Martin periodinane (452 g, 1.07 mmol). The suspension was stirred at 10° C. for 1 h, then allowed to warm to r.t. over 1 h. The reaction mixture was poured into saturated aqueous sodium hydrogen carbonate solution (~1 L) and stirred until gas evolution had ceased. Aqueous sodium thiosulfate solution (10%) was added, and the mixture was stirred for 1 h. The layers were separated and the aqueous phase was extracted with DCM. The organic layers were combined and dried (Na$_2$SO$_4$), then filtered and concentrated in vacuo. The resulting crude yellow oil was purified by flash column chromatography on silica (gradient elution with 0-20% EtOAc in heptane) to afford the title compound (186 g, 98%) as a colourless oil. $\delta_H$ (400 MHz, CDCl$_3$) 3.25-3.13 (m, 2H), 3.03-2.90 (m, 2H), 1.59 (s, 3H), 0.89 (s, 9H), 0.11 (s, 6H).

Intermediate 22

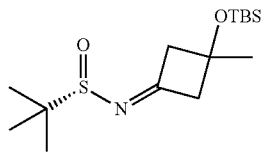 [SMILES: CC1(O[Si](C)(C)C(C)(C)C)CC(=N[S@@](=O)C(C)(C)C)C1]

(S)—N-{3-[tert-Butyl(dimethyl)silyl]oxy-3-methylcyclobutylidene}-2-methylpropane-2-sulfinamide To a solution of Intermediate 21 (186 g, 0.87 mol) in THF (2 L) was added (S)-(-)-tert-butylsulfinamide (126 g, 1.04 mol), followed by titanium(IV) ethoxide (367 mL, 1.74 mol). The reaction mixture was stirred overnight at r.t., then concentrated in vacuo. The residue was diluted with acetonitrile. Water (47 mL) was added and the reaction mixture was stirred for 10 minutes, then filtered over kieselguhr and rinsed with acetonitrile. The filtrate was concentrated in vacuo. The resulting crude yellow oil (264 g) was purified by flash column chromatography on silica (10% EtOAc in heptane) to afford the title compound (223 g, 81%) (~1:1 mixture of isomers) as a colourless oil. $\delta_H$ (400 MHz, CDCl$_3$) 3.59-3.41 (m, 1H), 3.34-3.11 (m, 2H), 3.05-2.92 (m, 1H), 1.52-1.41 (m, 3H), 1.21 (s, 9H), 0.85 (s, 9H), 0.06 (s, 6H). LCMS [M+H]$^+$ 318, RT 2.34 minutes (Method 6).

Intermediate 23

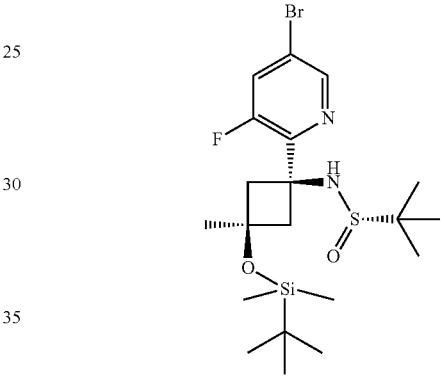

(S)—N-{cis-1-(5-Bromo-3-fluoropyridin-2-yl)-3-[tert-butyl(dimethyl)silyl]oxy-3-methylcyclobutyl}-2-methylpropane-2-sulfinamide A three-necked round-bottomed flask (2 L) was charged with 2,5-dibromo-3-fluoropyridine (26.9 g, 106 mmol) and DCM (750 mL). The resulting solution was cooled with dry ice/isopropanol to -70° C., then n-butyllithium (2.5M in hexanes; 46 mL, 115 mmol) was added dropwise, to afford a dark solution at -50° C. The temperature was lowered to -66° C. and a solution of Intermediate 22 (30.5 g, 96 mmol) in DCM (150 mL) was added dropwise. After addition, the mixture was stirred for 1.5 h, by which time the temperature had risen to -30° C. The reaction mixture was quenched with saturated aqueous ammonium chloride solution, and water was added to dissolve the precipitated salts. The layers were separated and the aqueous layer was extracted with DCM. The combined organic layers were washed with brine and dried (Na$_2$SO$_4$), then filtered and concentrated in vacuo. The resulting crude dark brown oil (49.7 g) was purified by flash column chromatography on silica (gradient elution with 10-60% EtOAc in heptane) to afford the title compound (9.71 g, 21%). $\delta_H$ (400 MHz, CDCl$_3$) 8.47-8.41 (m, 1H), 7.56 (dd, J 9.9, 1.9 Hz, 1H), 3.91 (s, 1H), 3.35 (dd, J 12.6, 3.6 Hz, 1H), 2.97-2.87 (m, 1H), 2.73 (d, J 12.6 Hz, 1H), 2.54 (d, J 12.6 Hz, 1H), 1.15 (s, 9H), 1.11 (s, 3H), 0.90 (s, 9H), 0.10 (s, 6H). LCMS [M+H]$^+$ 493/495 (Br-pattern), RT 2.50 minutes (Method 6).

Intermediate 24

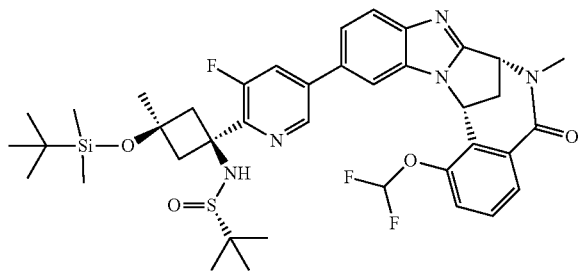 [SMILES: CN1C(=O)c2cccc(OC(F)F)c2[C@H]2C[C@@H]1c1nc3ccc(-c4cnc([C@]5(N[S@@](=O)C(C)(C)C)C[C@@](C)(O[Si](C)(C)C(C)(C)C)C5)c(F)c4)cc3n12]

(S)—N-(cis-3-[tert-Butyl(dimethyl)silyl]oxy-1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-3-methylcyclobutyl)-2-methylpropane-2-sulfinamide A three-necked round-bottomed flask (2 L) was charged with Intermediate 3 (25.6 g, 65.7 mmol), potassium acetate (16.1 g, 164 mmol), bis(pinacolato)diboron (20.0 g, 79 mmol) and anhydrous 1,4-dioxane (400 mL). The reaction mixture was evacuated and back-filled three times with argon. Tris(dibenzylideneacetone)dipalladium(0) (5 mol %, 3.01 g, 3.28 mmol) and XPhos (10 mol %, 3.13 g, 6.57 mmol) were added. The apparatus was evacuated and back-filled twice with argon, then placed in a preheated oil bath at 110° C. for 2.5 h. The reaction mixture was cooled to r.t. and Intermediate 23 (32.4 g, 65.7 mmol), dissolved in 1,4-dioxane (400 mL), was added. Tripotassium phosphate (20.9 g, 99 mmol) and water (200 mL) were added, followed by [1,1'-bis(diphenylphosphino)-ferrocene]dichloropalladium(II) (5 mol %, 2.40 g, 3.28 mmol). The reaction mixture was evacuated and back-filled twice with argon, then placed in a preheated oil bath at 115° C. for 1 h. The reaction mixture was cooled to r.t., then trithiocyanuric acid (5.24 g, 29.6 mmol) and activated charcoal (12 g) were added. The mixture was stirred overnight, then filtered through a pad of kieselguhr. The filter pad was rinsed with EtOAc and MeOH. The filtrate was diluted with water (600 mL) and the layers were separated. The aqueous layer was extracted with EtOAc (2×400 mL). The combined organic layers were washed with brine and dried (Na$_2$SO$_4$), then filtered and concentrated in vacuo. The resulting crude dark thick semi-solid (~130 g) was purified by flash column chromatography on silica (gradient elution with 0-20% MeOH in EtOAc), followed by repurification by flash column chromatography on silica (0-10% MeOH in EtOAc), to afford the title compound (44.6 g, 88%). 6.11 (400 MHz, CDCl$_3$) 8.63 (t, J1.5 Hz, 1H), 8.52-8.48 (m, 1H), 7.79 (d, J 8.5 Hz, 1H), 7.69 (d, J1.3 Hz, 1H), 7.56 (dd, J11.9, 1.7 Hz, 1H), 7.46 (dd, J8.5, 1.7 Hz, 1H), 7.43 (t, J8.2 Hz, 1H), 7.35 (d, J8.1 Hz, 1H), 6.88 (t, J 72.7 Hz, 1H), 6.28 (d, J7.2 Hz, 1H), 4.98 (d, J7.1 Hz, 1H), 4.00 (s, 1H), 3.52 (s, 3H), 3.51-3.40 (m, 1H), 3.07-2.99 (m, 1H), 2.89 (d, J13.6 Hz, 1H), 2.78 (d, J12.5 Hz, 1H), 2.62 (d, J12.6 Hz, 1H), 1.63 (s, 1H), 1.17 (s, 9H), 1.16 (s, 3H), 0.92 (s, 9H), 0.12 (s, 6H). LCMS [M+H]$^+$ 768, RT 2.44 minutes (Method 6).

Intermediate 25

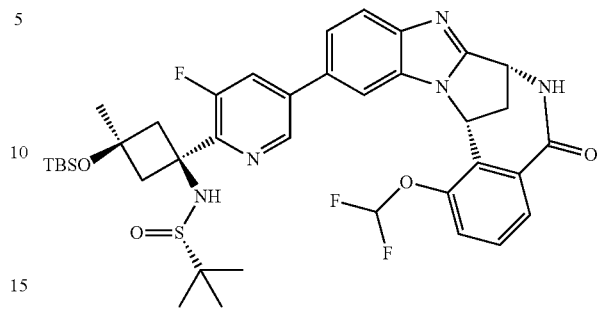

(S)—N-(cis-3-[tert-Butyl(dimethyl)silyl]oxy-1-{5-[(7R,14R)-1-(difluoromethoxy)-5-oxo-5,6,7,14-tetrahydro-7,14-methanobenzimidazo[1,2-b][2,5]benzodiazocin-11-yl]-3-fluoropyridin-2-yl}-3-methylcyclobutyl)-2-methylpropane-2-sulfinamide (7R,14R)-1-(Difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (WO 2016/050975, Intermediate 171) (1.3 g, 2.78 mmol), Intermediate 23 (900 mg, 1.82 mmol) and potassium phosphate tribasic (1.58 g, 7.29 mmol) were suspended in a mixture of 1,4-dioxane (22 mL) and water (2 mL). The reaction mixture was degassed three times with nitrogen, then tris(dibenzylideneacetone)dipalladium(0) (90 mg, 0.095 mmol) was added. The reaction mixture was further degassed with nitrogen and heated at 120° C. for 2.5 h. The mixture was diluted with water and extracted twice with EtOAc. The organic phases were combined and dried (sodium sulphate), then filtered and concentrated in vacuo. The crude residue was purified by flash column chromatography on silica (gradient elution with 0-100% EtOAc/hexane, followed by 0-10% MeOH/DCM) to afford the title compound (930 mg, 65%). LCMS (ES+) [M+H]$^+$ 754.2, RT 3.26 minutes (Method 4).

Intermediate 26

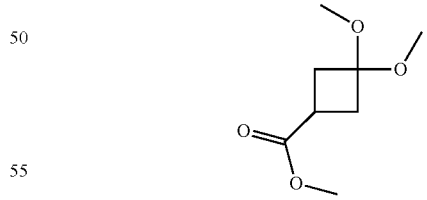

Methyl 3,3-dimethoxycyclobutanecarboxylate

Methyl 3-oxocyclobutanecarboxylate (45 g, 394 mmol), trimethyl orthoformate (259 mL, 2.37 mol) and p-toluenesulfonic acid monohydrate (7.50 g, 39.4 mmol) were combined in MeOH (500 mL). The solution was stirred at reflux for 2 h, then cooled to r.t. and concentrated in vacuo. The residue was dissolved in diethyl ether (500 mL) and washed with saturated aqueous sodium hydrogen carbonate solution (500 mL). The aqueous phase was extracted with diethyl ether (500 mL). The combined organic layers were washed with brine and dried (Na$_2$SO$_4$), then filtered and concentrated in vacuo, to afford the title compound (74.4 g). $\delta_H$ (400 MHz, CDCl$_3$) 3.70 (s, 3H), 3.17 (s, 3H), 3.15 (s, 3H), 2.94-2.83 (m, 1H), 2.48-2.34 (m, 4H).

Intermediate 27

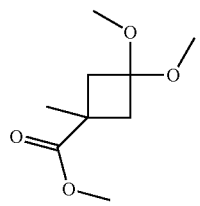

Methyl 3,3-dimethoxy-1-methylcyclobutanecarboxylate n-Butyllithium in hexanes (2.5M, 133 mL, 332 mmol) was added to a cooled solution of diisopropylamine (56 mL, 398 mmol) in THF (1 L) at −78° C. The mixture was stirred for 15 minutes prior to the dropwise addition of Intermediate 26 (68 g, 332 mmol) in THF (50 mL). The reaction mixture was stirred for 30 minutes prior to the dropwise addition of iodomethane (41 mL, 664 mmol), which caused the internal temperature to increase to −60° C. The reaction mixture was stirred at −78° C. for 30 minutes, then warmed to ambient temperature. The reaction mixture was poured into saturated aqueous ammonium chloride solution (1 L) and was extracted with diethyl ether (2×500 mL). The combined organic layers were washed with brine and dried (Na$_2$SO$_4$), then filtered and concentrated in vacuo. The crude residue (64.7 g) was purified by flash column chromatography on silica (gradient elution with 10-40% EtOAc in heptane) to afford the title compound (52.5 g). $\delta_H$ (400 MHz, CDCl$_3$) 3.71 (s, 3H), 3.16 (s, 3H), 3.13 (s, 3H), 2.67-2.58 (m, 2H), 2.10-2.01 (m, 2H), 1.44 (s, 3H).

Intermediate 28

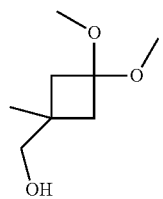

(3,3-Dimethoxy-1-methylcyclobutyl)methanol

To a solution of Intermediate 27 (42 g, 224 mmol) in THF (800 mL), cooled in an ice bath, was added 2.4M lithium aluminium hydride solution in THF (94 mL, 235 mmol). The reaction mixture was stirred at r.t. for 60 minutes. Water (8 mL) was added dropwise, followed by 10% aqueous sodium hydroxide solution (8 mL). To the suspension was added water (24 mL) and the mixture was stirred. Sodium sulphate was added and the granular suspension was filtered. The filtrate was rinsed with diethyl ether, and the combined filtrate was concentrated in vacuo, to afford the title compound (38 g, 15%) as a light oil. $\delta_H$ (400 MHz, CDCl$_3$) 3.50 (d, J5.6 Hz, 2H), 3.15 (s, 3H), 3.14 (s, 3H), 2.11 (d, J 13.2 Hz, 2H), 1.94-1.82 (m, 2H), 1.19 (s, 3H). GCMS [M-CH$_3$O]$^+$129, RT 2.325 (90.2%) (Method 12).

Intermediate 29

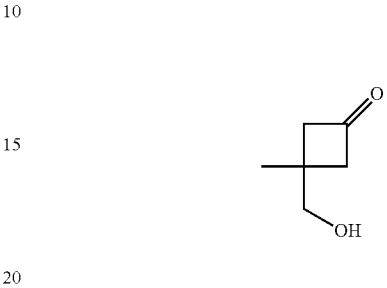

3-(Hydroxymethyl)-3-methylcyclobutanone

To a stirred solution of Intermediate 28 (44.8 g, 280 mmol) in acetone (600 mL) and water (200 mL) was added p-toluenesulfonic acid monohydrate (53.2 g, 280 mmol). The reaction mixture was heated at 65° C. for 1 h, then cooled to r.t. The acetone was removed by concentration in vacuo. The resulting mixture was diluted with DCM and washed with aqueous sodium hydrogen carbonate solution. The aqueous layer was back-extracted three times with DCM. The combined organic layers were dried (MgSO$_4$), then filtered and concentrated in vacuo, to afford the title compound (30.8 g, 78%). $\delta_H$ (400 MHz, CDCl$_3$) 3.69 (d, J5.1 Hz, 2H), 3.09-2.97 (m, 2H), 2.76-2.64 (m, 2H), 1.36 (s, 3H).

Intermediate 30

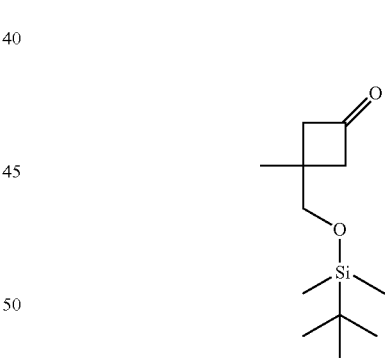

3-({[tert-Butyl(dimethyl)silyl]oxy}methyl)-3-methylcyclobutanone

Imidazole (0.63 g, 9.29 mmol) was added to a solution of Intermediate 29 (10.6 g, 55.0 mmol) in DMF (150 mL), then tert-butyl(chloro)dimethylsilane (24.9 g, 165 mmol) was added. The reaction mixture was stirred at r.t. overnight. Diethyl ether was added, followed by brine. The organic layer was separated and washed three times with brine. The organic layers were dried and concentrated in vacuo. The crude residue (62 g) was purified by flash column chromatography on silica (gradient elution with 0-10% EtOAc in heptane) to afford the title compound (59.5 g) as a yellow oil. δ$_H$ (400 MHz, CDCl$_3$) 3.59 (s, 2H), 3.08-2.98 (m, 2H), 2.66-2.56 (m, 2H), 1.30 (s, 3H), 0.89 (s, 9H), 0.06 (s, 6H).

Intermediate 31

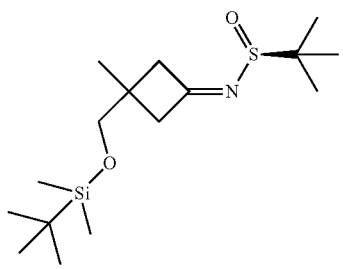 [SMILES: CC1(CO[Si](C)(C)C(C)(C)C)CC(=N[S@@](=O)C(C)(C)C)C1]

(S)—N-[3-({[tert-Butyl(dimethyl)silyl]oxy}methyl)-3-methylcyclobutylidene]-2-methyl-propane-2-sulfinamide To a solution of Intermediate 30 (54.5 g, 205 mmol) in THF (500 mL) were added (S)-2-methylpropane-2-sulfinamide (29.8 g, 246 mmol) and titanium(IV) ethoxide (87 mL, 410 mmol). The reaction mixture was stirred overnight at r.t., then concentrated in vacuo. The residue was diluted with acetonitrile, then water (47 mL) was added. The mixture was stirred for 10 minutes, then filtered over kieselguhr and rinsed with acetonitrile. The filtrate was concentrated in vacuo. The resulting crude yellow oil (71.5 g) was purified by flash column chromatography on silica (gradient elution with 0-20% EtOAc in heptane) to afford the title compound (66.9 g, 98%) as a yellow oil (~1:1 mixture of isomers). δ$_H$ (400 MHz, CDCl$_3$) 3.50 (d, J 1.6 Hz, 2H), 3.46-3.38 (m, 0.5H), 3.24-3.00 (m, 2H), 2.92-2.82 (m, 0.5H), 2.71-2.55 (m, 1H), 1.29-1.19 (m, 12H), 0.90-0.88 (m, 9H), 0.05 (s, 6H).

Intermediate 32

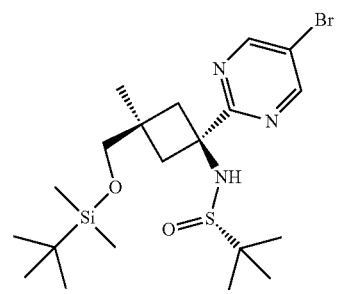 [SMILES: CC(C)(C)[S@](=O)N[C@]1(c2ncc(Br)cn2)C[C@](C)(CO[Si](C)(C)C(C)(C)C)C1]

(S)—N-[cis-1-(5-Bromopyrimidin-2-yl)-3-({[tert-butyl(dimethyl)silyl]oxy}methyl)-3-methylcyclobutyl]-2-methylpropane-2-sulfinamide A solution of 5-bromo-2-iodopyrimidine (58.6 g, 206 mmol) in DCM (500 mL) was cooled to −78° C. n-Butyllithium (2.5M in hexanes, 90 mL, 226 mmol) was added dropwise over 10 minutes, resulting in a thick suspension. The mixture was stirred for 40 minutes at −78° C. A solution of Intermediate 31 (56.8 g, 171 mmol) in DCM (500 mL) was added dropwise. The reaction mixture was stirred for 2.5 h at −78° C., then allowed to warm to r.t. and stirred for 1 h. The mixture was poured into saturated aqueous ammonium chloride solution and was stirred for 5 minutes. After dilution with water, the layers were separated. The aqueous layer was extracted twice with DCM. The organic layers were combined, washed with brine and dried (Na$_2$SO$_4$), then filtered and concentrated in vacuo. The crude residue was purified by flash column chromatography on silica (gradient elution with 1:1 to 0:1 heptane:EtOAc), followed by additional purification by flash column chromatography on silica (gradient elution with 20-80% EtOAc in heptane), to furnish the title compound (16 g, 17%). δ$_H$ (400 MHz, CDCl$_3$) 8.76 (s, 2H), 4.40 (s, 1H), 3.58 (d, J 9.6 Hz, 1H), 3.52 (d, J 9.5 Hz, 1H), 2.84 (d, J 12.7 Hz, 1H), 2.54-2.38 (m, 2H), 2.30 (d, J 12.3 Hz, 1H), 1.20 (s, 9H), 1.04 (s, 3H), 0.91 (s, 9H), 0.07 (s, 6H). LCMS [M+H]$^+$ 490/492 (Br-pattern), RT 2.49 minutes (Method 6).

Intermediate 33

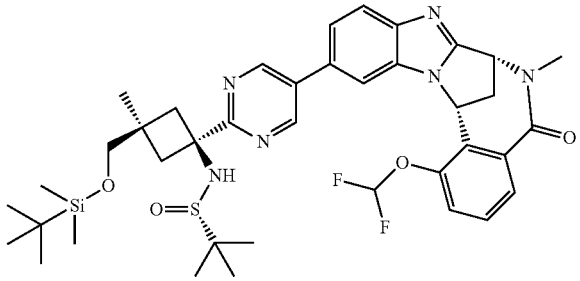 [SMILES: CN1C(=O)c2cccc(OC(F)F)c2[C@H]2C[C@@H]1c1nc3ccc(-c4cnc([C@]5(N[S@@](=O)C(C)(C)C)C[C@@](C)(CO[Si](C)(C)C(C)(C)C)C5)nc4)cc3n12]

(S)—N-[cis-3-({[tert-Butyl(dimethyl)silyl]oxy}methyl)-1-{5-[(7R,14R)-1-(difluoro-methoxy)-6-methyl-5-oxo-5,6,7,14-tetrahydro-7,14-methano-benzimidazo[1,2-b][2,5]-benzodiazocin-11-yl]pyrimidin-2-yl}-3-methylcyclobutyl]-2-methylpropane-2-sulfinamide A round-bottom flask (2 L) was charged with Intermediate 3 (11.1 g, 28.4 mmol), potassium acetate (6.97 g, 71.0 mmol), bis(pinacolato)diboron (8.65 g, 34.1 mmol) and 1,4-dioxane (170 mL). The apparatus was flushed three times with argon, then tris-(dibenzylideneacetone)dipalladium(0) (1.30 g, 1.42 mmol) and XPhos (1.35 g, 2.84 mmol) were added. The apparatus was evacuated and back-filled twice with argon, then heated at 115° C. for 3 h. The reaction mixture was cooled to r.t. Intermediate 32 (16.2 g, 28.4 mmol) dissolved in 1,4-dioxane (170 mL) was added, followed by water (70 mL) and anhydrous potassium phosphate tribasic (9.04 g, 42.6 mmol). The apparatus was again degassed twice with argon, then [1,1'-bis(diphenylphosphino)ferrocene]dichloro-palladium(II) (1.04 g, 1.42 mmol) was added. The reaction mixture was heated at 115° C. for 5 h, then stirred at r.t. overnight. Trithiocyanuric acid (2.27 g, 12.78 mmol) and activated charcoal (5.19 g) were added. The mixture was stirred at r.t. overnight, then diluted with water and EtOAc and filtered, washing the solids with EtOAc. The layers were separated and the aqueous layer was extracted twice with EtOAc. The organic layers were combined and washed with brine, then dried (Na$_2$SO$_4$), filtered and stirred overnight. The organic layers were concentrated in vacuo, and the residue was purified by flash column chromatography on silica (gradient elution with 0-10% MeOH in EtOAc) to afford the title compound (17.5 g, 81%). LCMS [M+H]+ 765, RT 2.46 minutes (Method 6).

Intermediate 34

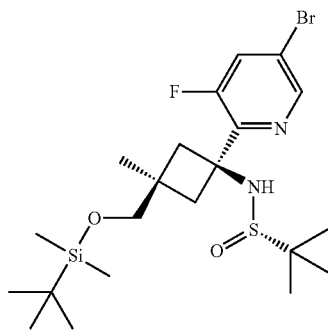 [SMILES: CC(C)(C)[S@](=O)N[C@]1(c2ncc(Br)cc2F)C[C@](C)(CO[Si](C)(C)C(C)(C)C)C1]

(S)—N-[cis-1-(5-Bromo-3-fluoropyridin-2-yl)-3-({ [tert-butyl(dimethyl)silyl]oxy}methyl)-3-methylcyclobutyl]-2-methylpropane-2-sulfinamide 2,5-Dibromo-3-fluoropyridine (2.4 g, 9.23 mmol) was dissolved in DCM (120 mL) and the reaction mixture was cooled to −65° C. in an acetone-dry ice bath. n-Butyllithium (2.5M in hexanes, 3.8 mL, 9.5 mmol) was added dropwise and the mixture was stirred at −65° C. for 15 minutes. Intermediate 31 (2.4 g, 7.2 mmol) in DCM (20 mL) was added. The reaction mixture was stirred at −65° C. for 1 h, then warmed to r.t. and stirred for 2 h. The reaction mixture was quenched with aqueous ammonium chloride solution at 0° C. and was extracted twice with DCM. The organic phases were combined and concentrated in vacuo, then purified by flash column chromatography on silica (gradient elution with 0-50% EtOAc/hexane) to afford the title compound (1.15 g, 31%). $\delta_H$ (300 MHz, CDCl$_3$) 8.47 (dd, J1.9, 1.2 Hz, 1H), 7.56 (dd, J9.9, 1.9 Hz, 1H), 3.85 (s, 1H), 3.60-3.46 (m, 2H), 2.87-2.73 (m, 1H), 2.54-2.47 (m, 2H), 2.47-2.38 (m, 1H), 1.16 (s, 9H), 0.96 (s, 3H), 0.94 (s, 9H), 0.09 (s, 6H).

Intermediate 35

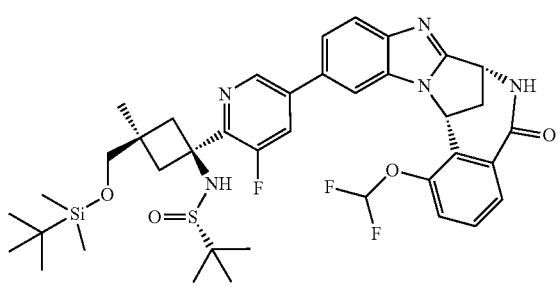 [SMILES: CC(C)(C)[S@](=O)N[C@]1(c2ncc(-c3ccc4nc5n(c4c3)[C@@H]3C[C@H]5NC(=O)c4cccc(OC(F)F)c43)cc2F)C[C@](C)(CO[Si](C)(C)C(C)(C)C)C1]

(S)—N-[cis-3-({[tert-Butyl(dimethyl)silyl]oxy}methyl)-1-{5-[(7R,14R)-1-(difluoro-methoxy)-5-oxo-5,6,7,14-tetrahydro-7,14-methanobenzimidazo[1,2-b][2,5]-benzodiazocin-11-yl]-3-fluoropyridin-2-yl}-3-methylcyclobutyl]-2-methylpropane-2-sulfinamide (7R,14R)-1-(Difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (WO 2016/050975, Intermediate 171) (405 mg, 0.87 mmol), Intermediate 34 (400 mg, 0.79 mmol), potassium phosphate tribasic (734 mg, 3.39 mmol) and tricyclohexylphosphonium tetrafluoroborate (40 mg, 0.11 mmol) were suspended in a mixture of 1,4-dioxane (10 mL) and water (1 mL). The mixture was degassed three times with nitrogen prior to the addition of tris(dibenzylideneacetone)dipalladium(0) (40 mg, 0.042 mmol). The mixture was further degassed with nitrogen and heated at 110° C. for 2.5 h. The reaction mixture was diluted with water and extracted twice with EtOAc. The combined organic phases were dried (Na$_2$SO$_4$), filtered and concentrated in vacuo. The crude residue was purified by flash column chromatography on silica (gradient elution with 0-100% EtOAc/hexane, followed by 0-10% MeOH/DCM) to afford the title compound (280 mg, 46%). LCMS (ES+) [M+H]+ 768.2, RT 3.42 minutes (Method 4).

Intermediate 36

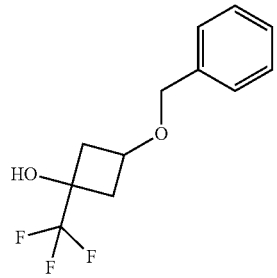 [SMILES: OC1(C(F)(F)F)CC(OCc2ccccc2)C1]

3-(Benzyloxy)-1-(trifluoromethyl)cyclobutan-1-ol

TBAF in THF (1M, 2.84 mL) was added dropwise to a stirred solution of 3-(benzyloxy)cyclobutan-1-one (5 g, 28.4 mmol) and trimethyl(trifluoromethyl)silane (5.03 mL, 34.1 mmol) in THF (50 mL) at 0° C. (external temperature). The resulting mixture was stirred at 0° C. for 2 h, then overnight at r.t. Further TBAF in THF (25.5 mL) was added and the mixture was stirred at r.t. for 2 h. Water (50 mL) was added and the mixture was poured onto brine (50 mL). The residue was extracted with EtOAc (3×75 mL). The combined organic phases were washed with brine (25 mL) and dried (MgSO$_4$), then filtered and concentrated in vacuo. The resulting crude orange oil was purified by flash column chromatography on silica (gradient elution with 0-100% EtOAc in heptanes) to afford the title compound (6.5 g, 92%) as a pale orange oil. $\delta_H$ (250 MHz, CDCl$_3$) 7.42-7.27 (m, 5H), 4.44 (s, 2H), 3.88 (p, J 6.7 Hz, 1H), 2.91-2.74 (m, 2H), 2.56 (s, 1H), 2.32-2.15 (m, 2H).

Intermediate 37

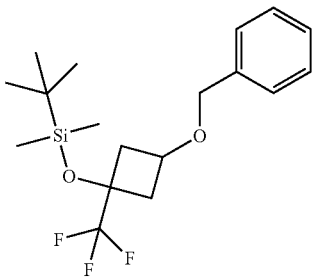 [SMILES: CC(C)(C)[Si](C)(C)OC1(C(F)(F)F)CC(OCc2ccccc2)C1]

[3-(Benzyloxy)-1-(trifluoromethyl)cyclobutoxy](tert-butyl)dimethylsilane tert-Butyldimethylsilyl trifluoromethanesulfonate (6.16 mL, 30 mmol) was added dropwise to a stirred solution of Intermediate 36 (6 g, 24.4 mmol) and 2,6-dimethyl-pyridine (8.16 mL, 70 mmol) in DCM (60 mL) at −78° C. The mixture was stirred at −78° C. for 30 minutes, then allowed to warm slowly to r.t. overnight. The mixture was treated with saturated aqueous sodium hydrogen carbonate solution (60 mL) and the layers were separated. The aqueous phase was further extracted with DCM (60 mL). The combined organic phase was dried (MgSO$_4$), filtered and concentrated in vacuo. The residue was purified by flash column chromatography on silica (gradient elution with 0-100% EtOAc in heptanes) to afford the title compound (8.14 g, 93%) as a pale yellow oil. $\delta_H$ (250 MHz, CDCl$_3$) 7.45-7.27 (m, 5H), 4.43 (s, 2H), 3.82 (p, J6.8 Hz, 1H), 2.92-2.74 (m, 2H), 2.35-2.17 (m, 2H), 0.90 (s, 9H), 0.14 (s, 6H).

Intermediate 38

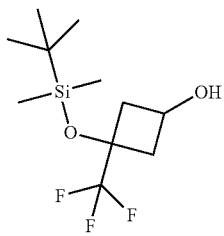 [SMILES: CC(C)(C)[Si](C)(C)OC1(C(F)(F)F)CC(O)C1]

3-{[tert-Butyl(dimethyl)silyl]oxy}-3-(trifluoromethyl)cyclobutan-1-ol

A stirred mixture of Intermediate 37 (8.14 g, 22.6 mmol) and 10% palladium on carbon (50% in water, 2.41 g, 11.3 mmol) in ethanol (163 mL) was placed under an atmosphere of hydrogen gas. The reaction mixture was stirred at r.t. for 24 h, then filtered through celite. The filter cake was washed with MeOH (3×50 mL). The filtrate was concentrated in vacuo. The resulting dark residue was filtered over celite and the filter cake was washed with MeOH (3×50 mL). The filtrate was concentrated in vacuo to afford the title compound (6.2 g, 98%) as an opaque light yellow wax. $\delta_H$ (250 MHz, CDCl$_3$) 4.21-4.01 (m, 1H), 2.99-2.84 (m, 2H), 2.34-2.14 (m, 2H), 1.89 (s, 1H), 0.90 (s, 9H), 0.14 (s, 6H).

Intermediate 39

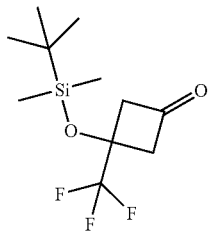 [SMILES: CC(C)(C)[Si](C)(C)OC1(C(F)(F)F)CC(=O)C1]

3-{[tert-Butyl(dimethyl)silyl]oxy}-3-(trifluoromethyl)cyclobutan-1-one

Dess-Martin periodinane (11.3 g, 26.9 mmol) was added to a stirred solution of Intermediate 38 (6.2 g, 22.2 mmol) in DCM (175 mL) at r.t. The mixture was stirred at r.t. overnight, then diluted with DCM (50 mL) and filtered over a pad of celite. The filter cake was washed with further DCM (25 mL), and the filtrate was poured onto saturated aqueous sodium hydrogen carbonate solution (100 mL). The layers were separated, and the aqueous phase was further extracted with DCM (50 mL). The combined organic phases were dried (MgSO$_4$), filtered and concentrated in vacuo. The resulting waxy crystalline solid was purified by flash column chromatography on silica (gradient elution with 0-100% EtOAc in heptanes) to afford the title compound (5.71 g, 86%) as a pale yellow oil. $\delta_H$ (250 MHz, CDCl$_3$) 3.61-3.40 (m, 2H), 3.31-3.15 (m, 2H), 0.91 (s, 9H), 0.20-0.13 (m, 6H).

Intermediate 40

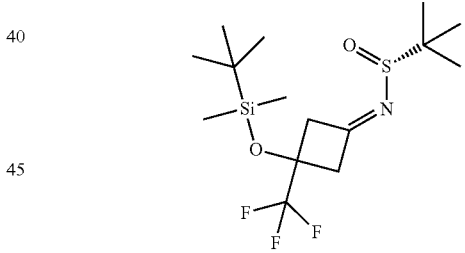

(R)—N-(3-{[tert-Butyl(dimethyl)silyl]oxy}-3-(trifluoromethyl)cyclobutylidene)-2-methyl-propane-2-sulfinamide Titanium(IV) ethoxide (24.4 mL, 38.1 mmol) was added to a stirred solution of Intermediate 39 (5 g, 18.6 mmol) in THF (100 mL) at r.t. under nitrogen. The mixture was stirred for 10 minutes, then (R)-2-methylpropane-2-sulfinamide (4.52 g, 37.3 mmol) was added. The mixture was heated at 65° C. for 1.5 h, then cooled to r.t. The mixture was diluted with brine (70 mL), EtOAc (200 mL) and water (35 mL), then stirred vigorously for 15 minutes. The organic layer was decanted and the remaining emulsion was filtered over filter paper. The filtrate was further extracted with EtOAc (100 mL). The combined organic phases were washed with brine (50 mL) and dried (MgSO$_4$), then filtered and concentrated in vacuo. The resulting crude yellow syrup was purified by flash column chromatography on silica (gradient elution with 0-50% EtOAc in heptanes) to afford the title compound (5.5 g, 80%) as a light yellow oil. δ_H (250 MHz, CDCl₃) 4.18-3.11 (m, 4H), 1.29-1.20 (m, 9H), 0.90 (s, 9H), 0.15 (s, 6H). LCMS (ESI) [M+H]⁺ 372.15, RT 1.52 minutes (Method 8).

Intermediate 41

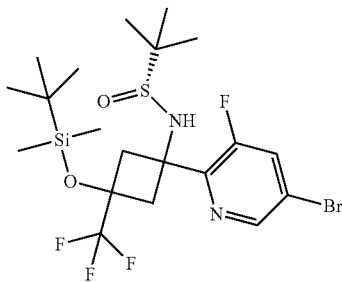 [SMILES: CC(C)(C)[S@@](=O)NC1(c2ncc(Br)cc2F)CC(O[Si](C)(C)C(C)(C)C)(C(F)(F)F)C1]

(R)—N-[1-(5-Bromo-3-fluoropyridin-2-yl)-3-{[tert-butyl(dimethyl)silyl]oxy}-3-(trifluoro-methyl)cyclobutyl]-2-methylpropane-2-sulfinamide n-Butyllithium in hexanes (2.5M, 3.47 mL, 8.66 mmol) was added dropwise to a stirred solution of 2,5-dibromo-3-fluoropyridine (2.17 g, 8.51 mmol) in DCM (140 mL) at −70° C. (internal temperature). After stirring for 15 minutes, a solution of Intermediate 40 (2.75 g, 7.4 mmol) in DCM (14 mL) was added dropwise. Stirring was maintained at −70° C. for 2 h. The mixture was slowly warmed to r.t. over approximately 1.5 h, then re-cooled to 0° C. Saturated aqueous ammonium chloride solution (100 mL) was added and the mixture was stirred vigorously for 10 minutes. The layers were separated and the aqueous phase was further extracted with DCM (2×100 mL). The combined organic phases were dried (MgSO₄), filtered and concentrated in vacuo. The crude residue was purified by flash column chromatography on silica (gradient elution with 0-50% EtOAc in heptanes) to afford the title compound (1.68 g, 42%) as a pale orange gum. δ_H (250 MHz, CDCl₃) 8.46 (d, J6.7 Hz, 1H), 7.65-7.50 (m, 1H), 3.86 (s, 1H), 3.50-3.33 (m, 1H), 3.13-2.89 (m, 2H), 2.88-2.59 (m, 1H), 1.19-1.11 (m, 9H), 0.95-0.69 (m, 9H), 0.24 to −0.07 (m, 6H). LCMS (ESI) [M+H]⁺ 547.2, RT 1.91 minutes (Method 9).

Intermediate 42

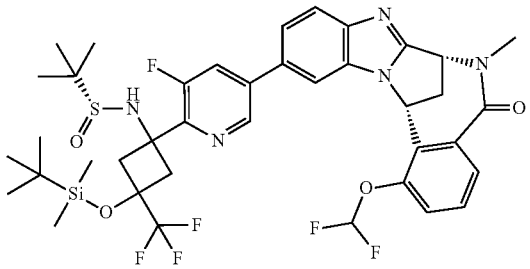 [SMILES: CN1C(=O)c2cccc(OC(F)F)c2[C@H]2C[C@@H]1c1nc3ccc(-c4cnc(C5(N[S@](=O)C(C)(C)C)CC(O[Si](C)(C)C(C)(C)C)(C(F)(F)F)C5)c(F)c4)cc3n12]

(R)—N-[3-{[tert-Butyl(dimethyl)silyl]oxy}-1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-3-(trifluoromethyl)cyclobutyl]-2-methylpropane-2-sulfinamide Intermediate 4 (886 mg, 1.84 mmol) was added to a stirred solution of Intermediate 41 (840 mg, 1.53 mmol) in 1,4-dioxane (10 mL) at r.t. in a sealable pressure vessel. The mixture was treated with 2M aqueous potassium carbonate solution (2.3 mL) and purged with nitrogen for 15 minutes. XPhos (73 mg, 0.15 mmol) and XPhos Pd G2 (121 mg, 0.15 mmol) were added and the vessel was sealed. The mixture was stirred at 100° C. for 4 h, then cooled to r.t. The dark mixture was diluted with EtOAc (30 mL) and poured onto brine (50 mL). The layers were separated and the aqueous phase was further extracted with EtOAc (2×25 mL). The combined organic phase was washed with brine (25 mL) and dried (MgSO₄), then filtered and concentrated in vacuo. The resulting dark residue was purified by flash column chromatography on silica (gradient elution with 0-10% MeOH in DCM). The resulting crude pale brown foam was purified by further flash column chromatography on silica (gradient elution with 0-100% EtOAc in heptanes) to afford the title compound (1.00 g, 76%) as an off-white foam. δ_H (250 MHz, CDCl₃) 8.64 (dd, J3.4, 1.7 Hz, 1H), 8.49 (d, J8.1 Hz, 1H), 7.82-7.30 (m, 6H), 7.19-6.53 (m, 1H), 6.35-6.21 (m, 1H), 5.04-4.94 (m, 1H), 3.94 (s, 1H), 3.53 (s, 3H), 3.49-3.39 (m, 1H), 3.17-2.67 (m, 4H), 1.30-1.22 (m, 1H), 1.22-1.12 (m, 9H), 1.00-0.63 (m, 9H), 0.25 to −0.05 (m, 6H). LCMS (ESI) [M+H]⁺ 822.4, RT 2.22/2.26 minutes (Method 10).

Intermediate 43

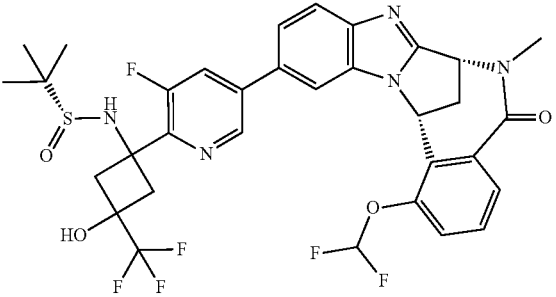 [SMILES: CN1C(=O)c2cccc(OC(F)F)c2[C@H]2C[C@@H]1c1nc3ccc(-c4cnc(C5(N[S@](=O)C(C)(C)C)CC(O)(C(F)(F)F)C5)c(F)c4)cc3n12]

(R)—N-[1-{5-[(7R,14R)-1-(Difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-3-hydroxy-3-(trifluoromethyl)cyclobutyl]-2-methylpropane-2-sulfinamide TBAF in THF (1M, 2.33 mL, 2.32 mmol) was added to a stirred solution of Intermediate 42 (1 g, 1.16 mmol) in THF (15 mL) at r.t. The mixture was warmed and stirred at 35° C. for 2 h. After cooling to r.t., the mixture was poured onto water (25 mL) and extracted with EtOAc (3×25 mL). The combined organic phase was washed with brine (30 mL) and dried (MgSO₄), then filtered and concentrated in vacuo. The resulting off-white solid (0.9 g) was suspended in DMSO-MeOH (1:1; 6 mL). The resulting thick paste was concentrated in vacuo to afford crude title compound (0.82 g) as an off-white solid, which was utilised without further purification. LCMS (ESI) [M+H]+ 708.4, RT 3.11 minutes (Method 11).

Intermediate 44

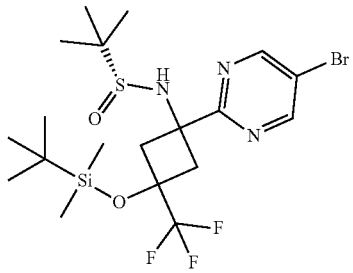 [SMILES: CC(C)(C)[S@@](=O)NC1(c2ncc(Br)cn2)CC(O[Si](C)(C)C(C)(C)C)(C(F)(F)F)C1]

(R)—N-[1-(5-Bromopyrimidin-2-yl)-3-{[tert-butyl(dimethyl)silyl]oxy}-3-(trifluoro-methyl)cyclobutyl]-2-methylpropane-2-sulfinamide n-Butyllithium in hexanes (2.5M, 5.09 mL, 12.7 mmol) was added dropwise to a stirred solution of 5-bromo-2-iodopyrimidine (3.56 g, 12.51 mmol) in DCM (230 mL) at −70° C. (internal temperature). After stirring for 15 minutes, a solution of Intermediate 40 (4.04 g, 10.9 mmol) in DCM (20 mL) was added dropwise. Stirring was maintained at −70° C. for 2 h. Whilst at this temperature, the mixture was quenched with saturated aqueous ammonium chloride solution (150 mL) and the resulting slurry was warmed slowly to r.t. The layers were separated and the aqueous phase was further extracted with DCM (100 mL). The combined organic phase was dried (MgSO₄), filtered and concentrated in vacuo. The resulting dark brown oil/solid was purified by flash column chromatography on silica (gradient elution with 0-100% EtOAc in heptanes). Further purification of the resulting partially purified yellow oil by flash column chromatography on reverse phase silica (gradient elution with 10-100% acetonitrile in water spiked with 0.1% formic acid) afforded the title compound (0.51 g, 9%) as a pale orange oil. $\delta_H$ (250 MHz, CDCl₃) 8.81-8.74 (m, 2H), 4.48 (d, J33.1 Hz, 1H), 3.90-2.64 (m, 4H), 1.23-1.15 (m, 9H), 0.97-0.70 (m, 9H), 0.22 to −0.05 (m, 6H). LCMS (ESI) [M+H]+ 530/532, RT 1.53 minutes (Method 8).

Intermediate 45

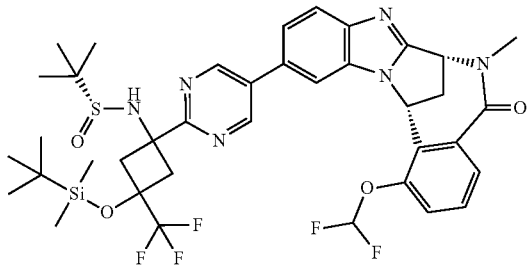 [SMILES: CN1C(=O)c2cccc(OC(F)F)c2[C@H]2C[C@@H]1c1nc3ccc(-c4cnc(C5(N[S@](=O)C(C)(C)C)CC(O[Si](C)(C)C(C)(C)C)(C(F)(F)F)C5)nc4)cc3n12]

(R)—N-[3-{[tert-Butyl(dimethyl)silyl]oxy}-1-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-pyrimidin-2-yl}-3-(trifluoromethyl)cyclobutyl]-2-methylpropane-2-sulfinamide Intermediate 4 (552 mg, 1.15 mmol) was added to a stirred solution of Intermediate 44 (507 mg, 0.96 mmol) in 1,4-dioxane (7 mL) at r.t. in a sealable pressure vessel. The mixture was treated with 2M aqueous potassium carbonate solution (1.44 mL) and the mixture was purged with nitrogen for 15 minutes. XPhos (46 mg, 0.1 mmol) and XPhos Pd G2 (75 mg, 0.1 mmol) were added and the vessel was sealed. The mixture was stirred at 100° C. for 4 h, then cooled to r.t. The dark mixture was diluted with EtOAc (30 mL) and poured onto brine (50 mL). The layers were separated and the aqueous phase was further extracted with EtOAc (2×25 mL). The combined organic phases were washed with brine (25 mL) and dried (MgSO₄), then filtered and concentrated in vacuo. The resulting dark residue (1.18 g) was purified by flash column chromatography on silica (gradient elution with 0-100% EtOAc in heptanes). The resulting crude pale orange foam was further purified by column chromatography on reverse phase silica (gradient elution with 10-100% acetonitrile in water spiked with 0.1% formic acid) to afford the title compound (0.61 g, 79%) as an off-white glass. $\delta_H$ (250 MHz, CDCl₃) 9.04-8.87 (m, 2H), 8.50 (d, J8.1 Hz, 1H), 7.92-7.79 (m, 1H), 7.71 (s, 1H), 7.56-7.31 (m, 3H), 6.89 (t, J 72.7 Hz, 1H), 6.31 (d, J7.2 Hz, 1H), 5.04 (d, J7.2 Hz, 1H), 4.66-4.40 (m, 1H), 3.64 (d, J 14.8 Hz, 1H), 3.52 (s, 3H), 3.20-2.70 (m, 5H), 1.36-1.14 (m, 9H), 1.02-0.66 (m, 9H), 0.26 to −0.11 (m, 6H). LCMS (ESI) [M+H]+ 805.4, RT 1.54 minutes (Method 8).

Intermediate 46

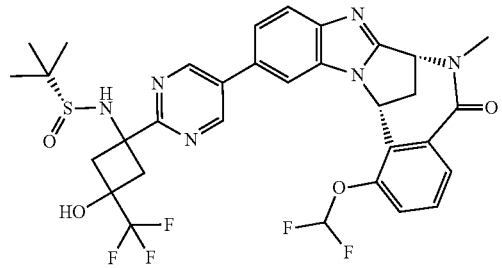 [SMILES: CN1C(=O)c2cccc(OC(F)F)c2[C@H]2C[C@@H]1c1nc3ccc(-c4cnc(C5(N[S@](=O)C(C)(C)C)CC(O)(C(F)(F)F)C5)nc4)cc3n12]

(R)—N-[1-{5-[(7R,14R)-1-(Difluoromethoxy)-6-methyl-5-oxo-5,6,7,14-tetrahydro-7,14-methanobenzimidazo[1,2-b][2,5]benzodiazocin-11-yl]pyrimidin-2-yl}-3-hydroxy-3-(trifluoromethyl)cyclobutyl]-2-methylpropane-2-sulfinamide TBAF in THF (1M, 1.52 mL) was added to a stirred solution of Intermediate 45 (0.61 g, 0.76 mmol) in THF (10 mL) at r.t. The mixture was stirred at r.t. overnight, then poured onto water (35 mL). The residue was extracted with EtOAc (3×35 mL). The combined organic phases were washed with water (30 mL) and brine (30 mL), then dried (MgSO₄), filtered and concentrated in vacuo, to give the title compound (0.474 g, 90%) as an off-white solid. $\delta_H$ (250 MHz, CD₃OD) 9.14-9.04 (m, 2H), 8.47-8.35 (m, 1H), 7.96-7.89 (m, 1H), 7.82 (d, J8.5 Hz, 1H), 7.65 (dd, J8.6, 1.7 Hz, 1H), 7.63-7.03 (m, 3H), 6.49 (d, J7.1 Hz, 1H), 5.26 (d, J7.1 Hz, 1H), 4.59 (s, 1H), 3.73-3.57 (m, 1H), 3.52 (s, 3H), 3.43-3.36 (m, 1H), 3.10-2.87 (m, 3H), 2.75 (d, J14.4 Hz, 1H), 1.33-1.19 (m, 9H). LCMS (ESI) [M+H]$^+$ 691.25, RT 1.10 & 1.13 minutes (Method 8).

Intermediate 47

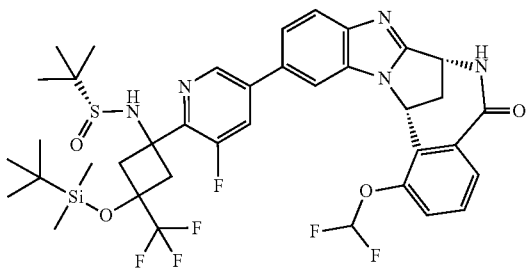 [SMILES: CC(C)(C)[S@@](=O)NC1(c2ncc(-c3ccc4nc5n(c4c3)[C@@H]3C[C@H]5NC(=O)c4cccc(OC(F)F)c43)cc2F)CC(O[Si](C)(C)C(C)(C)C)(C(F)(F)F)C1]

(R)—N-[3-{[tert-Butyl(dimethyl)silyl]oxy}-1-{5-[(7R,14R)-1-(difluoromethoxy)-5-oxo-5,6,7,14-tetrahydro-7,14-methanobenzimidazo[1,2-b][2,5]benzodiazocin-11-yl]-3-fluoro-pyridin-2-yl}-3-(trifluoromethyl)cyclobutyl]-2-methylpropane-2-sulfinamide To a stirred solution of Intermediate 41 (400 mg, 0.73 mmol) and (7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (WO 2016/050975, Intermediate 171) (383 mg, 0.8 mmol) in 1,4-dioxane (10 mL) was added 2M aqueous potassium carbonate solution (1.1 mL). The reaction mixture was degassed with nitrogen, then XPhos (35 mg, 0.07 mmol) and XPhos Pd G2 (57 mg, 0.07 mmol) were added. The reaction mixture was heated in a sealed tube at 100° C. for 2.5 h. The reaction mixture was allowed to cool, then diluted with EtOAc (50 mL) and washed with brine (2×25 mL). The organic layer was dried (Na$_2$SO$_4$), filtered and concentrated in vacuo. The crude residue was purified by flash column chromatography on silica (gradient elution with 0-100% EtOAc/heptanes followed by 0-20% MeOH/EtOAc), then by column chromatography on reverse phase silica (gradient elution with 10-100% acetonitrile/water+0.1% formic acid), to afford the title compound (469 mg, 72%) (4:5 mixture of cis/trans isomers) as a white solid. δ$_H$ (500 MHz, CDCl$_3$) 8.62 (dd, J 7.2, 1.6 Hz, 1H), 8.42 (dt, J 7.9, 1.8 Hz, 1H), 7.79 (dd, J8.3, 6.6 Hz, 1H), 7.66 (dd, J5.3, 1.4 Hz, 1H), 7.61-7.52 (m, 1H), 7.49-7.36 (m, 3H), 7.09 (t, J 5.9 Hz, 1H), 6.87 (t, J 72.6 Hz, 1H), 6.37 (dd, J 7.2, 4.2 Hz, 1H), 4.99-4.87 (m, 1H), 3.94 (s, 1H), 3.91-3.83 (m, 0.56H, major), 3.55-3.48 (m, 2H), 3.14-3.05 (m, 1H), 3.03-2.99 (m, 0.44H, minor), 2.90-2.86 (m, 1H), 2.86-2.69 (m, 1H), 1.18 (s, 4H, minor), 1.17 (s, 5H, major), 0.94 (s, 4H, minor), 0.70 (s, 5H, major), 0.19 (d, J 11.3 Hz, 2.67H, minor), −0.01 (d, J11.3 Hz, 3.33H, major).

Intermediate 48

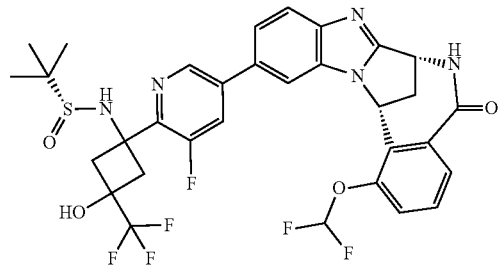 [SMILES: CC(C)(C)[S@@](=O)NC1(c2ncc(-c3ccc4nc5n(c4c3)[C@@H]3C[C@H]5NC(=O)c4cccc(OC(F)F)c43)cc2F)CC(O)(C(F)(F)F)C1]

(R)—N-[1-{5-[(7R,14R)-1-(Difluoromethoxy)-5-oxo-5,6,7,14-tetrahydro-7,14-methanobenzimidazo[1,2-b][2,5]benzodiazocin-11-yl]-3-fluoropyridin-2-yl}-3-hydroxy-3-(trifluoromethyl)cyclobutyl]-2-methylpropane-2-sulfinamide To a solution of Intermediate 47 (469 mg, 0.56 mmol) in THF (6 mL) was added TBAF in THF (1M, 1.11 mL). The reaction mixture was stirred at 35° C. for 2 h, then cooled, diluted with brine (50 mL) and extracted with EtOAc (2×50 mL). The combined organic layers were washed with brine (3×50 mL) and dried (Na$_2$SO$_4$), then filtered and concentrated in vacuo, to afford crude title compound (440 mg, quantitative) as an off-white powder, which was utilised without further purification. δ$_H$ (500 MHz, CDCl$_3$) 8.49 (d, J23.5 Hz, 1H), 8.41-8.28 (m, 1H), 7.67 (dd, J 31.2, 8.5 Hz, 1H), 7.57 (dd, J13.3, 1.4 Hz, 1H), 7.47 (ddd, J12.0, 6.2, 1.8 Hz, 1H), 7.39-7.26 (m, 3H), 7.10-7.00 (m, 1H), 6.78 (td, J 72.7, 4.2 Hz, 1H), 6.28 (d, J7.2 Hz, 1H), 4.86 (t, J 6.5 Hz, 1H), 4.43-4.04 (m, 1H), 3.52-3.33 (m, 3H), 3.06-2.55 (m, 4H), 1.11 (d, J4.1 Hz, 9H). LCMS (ESI) [M+H]$^+$ 694.3, RT 1.35 and 1.40 minutes (Method 9).

Intermediate 49

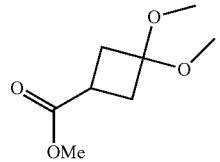

Methyl 3,3-dimethoxycyclobutanecarboxylate

Ethyl 3-oxocyclobutanecarboxylate (53 g, 372.8 mmol), trimethyl orthoformate (200 mL, 1830 mmol) and 4-methylbenzenesulfonic acid hydrate (1:1) (7.09 g, 37.3 mmol) were combined in methanol (500 mL) and heated under reflux, with stirring, for 1 h. The reaction mixture was cooled to r.t. and concentrated under reduced pressure. The residue was dissolved in diethyl ether (500 mL) and washed with saturated aqueous NaHCO$_3$ solution (400 mL). The aqueous phase was extracted with diethyl ether (500 mL). The combined organic phases were dried (MgSO$_4$), filtered and concentrated in vacuo. The residue was azeotroped with heptane, to remove the remaining trimethyl orthoformate, to afford the title compound (71.5 g, 99%) as light beige oil. δ$_H$ (500 MHz, CDCl$_3$) 3.69 (s, 3H), 3.17 (s, 3H), 3.15 (s, 3H), 2.88 (m, 1H), 2.48-2.32 (m, 4H).

Intermediate 50

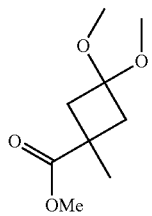

Methyl 3,3-dimethoxy-1-methylcyclobutanecarboxylate

Under a nitrogen atmosphere, 2M LDA solution (108.5 mL, 217 mmol in THF) was added to THF (300 mL) at −78° C. A solution of Intermediate 49 (90%, 35 g, 180.8 mmol) in THF (50 mL) was added dropwise over 25 minutes, maintaining the internal temperature at −78° C. After complete addition, the mixture was stirred for 30 minutes, then iodomethane (15 mL, 241 mmol) was added dropwise. The mixture was stirred at −78° C. for 30 minutes, then allowed to warm to r.t. over 1 h. The mixture was poured into saturated aqueous NH$_4$Cl solution (300 mL) and extracted with diethyl ether (2×500 mL). The combined organic phases were washed with brine and dried (Na$_2$SO$_4$), then filtered and evaporated to dryness. The residue was purified by flash column chromatography (40% EtOAc in heptane) to afford the title compound (23 g, 57%) as a light yellow oil. δ$_H$ (250 MHz, CDCl$_3$) 3.70 (s, 3H), 3.16 (s, 3H), 3.13 (s, 3H), 2.68-2.55 (m, 2H), 2.13-1.99 (m, 2H), 1.43 (s, 3H).

Intermediate 51

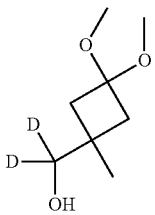

Dideuterio(3,3-dimethoxy-1-methylcyclobutyl)methanol

Under a nitrogen atmosphere, to a suspension of LiAlD$_4$ (5 g, 119 mmol) in THF (400 mL) at 0° C. (ice bath) was added dropwise a solution of Intermediate 50 (27.2 g, 118.5 mmol) in THF (100 mL). When the addition was complete, the reaction mixture was stirred at r.t. overnight, then cooled in an ice bath. Water (5 mL) was added dropwise with stirring. The suspension which formed was diluted with THF (150 mL), followed by the addition of 15% aqueous NaOH solution (5 mL) and water (15 mL). To the resulting suspension was added Na$_2$SO$_4$ (40 g), and the mixture was stirred for 30 minutes. The granular suspension was filtered and rinsed with diethyl ether, then the combined filtrates were concentrated under reduced pressure, to give the title compound (23.8 g, 99%) as a light yellow oil. δ$_H$ (250 MHz, CDCl$_3$) 3.22-3.07 (m, 6H), 2.17-2.03 (m, 2H), 1.93-1.78 (m, 2H), 1.18 (s, 3H).

Intermediate 52

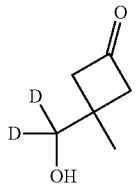

3-[Dideuterio(hydroxy)methyl]-3-methylcyclobutanone

To a stirred solution of Intermediate 51 (23.8 g, 117.3 mmol) in acetone (240 mL) and water (80 mL) was added 4-methylbenzenesulfonic acid hydrate (1:1) (5 g, 26.3 mmol). The reaction mixture was heated at 65° C. for 2 h, then allowed to stand at r.t. overnight. The acetone was removed under reduced pressure. The resulting mixture was basified with solid NaHCO$_3$ to pH 8 and extracted with DCM (5×130 mL). The combined organic layers were dried over Na$_2$SO$_4$ and filtered through a fritted funnel, then concentrated under reduced pressure, to afford the title compound (16 g, 94%) as a light brown oil. δ$_H$ (250 MHz, CDCl$_3$) 3.12-2.92 (m, 2H), 2.79-2.57 (m, 2H), 1.69 (s, 1H), 1.36 (s, 3H).

Intermediate 53

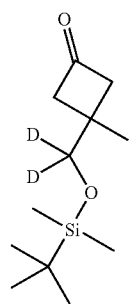 [SMILES: [2H]C([2H])(O[Si](C)(C)C(C)(C)C)C1(C)CC(=O)C1]

3-{[tert-Butyl(dimethyl)silyl]oxy(dideuterio)methyl}-3-methylcyclobutanone

To a solution of Intermediate 52 (16 g, 110 mmol) in DMF (100 mL) were added 1H-imidazole (15 g, 220 mmol) and tert-butyl(chloro)dimethylsilane (22 g, 146 mmol). The mixture was stirred at r.t. overnight, then diluted with diethyl ether (250 mL) and water (200 mL). The layers were separated, then the aqueous layer was extracted with diethyl ether (250 mL). The combined organic phases were washed with brine (3×80 mL) and dried over MgSO$_4$, then filtered and concentrated in vacuo, to afford the title compound (30 g, 97%) as a light brown oil. $\delta_H$ (250 MHz, CDCl$_3$) 3.13-2.94 (m, 2H), 2.70-2.51 (m, 2H), 1.29 (s, 3H), 0.89 (s, 9H), 0.06 (s, 6H).

Intermediate 54

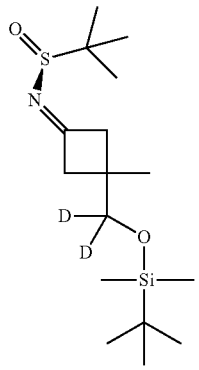 [SMILES: [2H]C([2H])(O[Si](C)(C)C(C)(C)C)C1(C)CC(=N[S@@](=O)C(C)(C)C)C1]

N-(3-{[tert-Butyl(dimethyl)silyl]oxy(dideuterio)methyl}-3-methylcyclobutylidene)-2-methylpropane-2-sulfinamide To a solution of Intermediate 53 (30 g, 107 mmol) in anhydrous THF (250 mL) under a nitrogen atmosphere was added (R)-2-methylpropane-2-sulfinamide (15.53 g, 128.1 mmol), followed by titanium(IV) ethoxide (50 mL, 202.7 mmol). The mixture was stirred at r.t. for 24 h. Further portions of (R)-2-methylpropane-2-sulfinamide (2.8 g, 23.1 mmol) and titanium(IV) ethoxide (5 mL, 20.27 mmol) were added to the reaction mixture, which was then stirred at 65° C. for 4 h. The reaction mixture was cooled to r.t. and water (13 mL) was added, followed by EtOAc (200 mL). The reaction mixture was filtered over celite and the solid was washed extensively with EtOAc. The filtrate was dried over Na$_2$SO$_4$, then filtered and evaporated in vacuo. The crude residue was purified by column chromatography (5-20% EtOAc in heptane) to afford the title compound (31.5 g, 84%) as a yellow oil. $\delta_H$ (500 MHz, CDCl$_3$) 3.47-3.16 (m, 1H), 3.13-2.83 (m, 2H), 2.71-2.55 (m, 1H), 1.25-1.21 (m, 12H), 0.91-0.87 (m, 9H), 0.05 (s, 6H) (1:1 mixture of E/Z isomers).

Intermediate 55

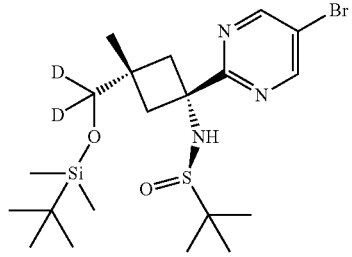 [SMILES: [2H]C([2H])(O[Si](C)(C)C(C)(C)C)[C@]1(C)C[C@@](N[S@](=O)C(C)(C)C)(c2ncc(Br)cn2)C1]

N-[1-(5-Bromopyrimidin-2-yl)-3-{[tert-butyl(dimethyl)silyl]oxy(dideuterio)methyl}-3-methylcyclobutyl]-2-methylpropane-2-sulfinamide Under a nitrogen atmosphere, a solution of 5-bromo-2-iodopyrimidine (71.2 g, 250 mmol) in anhydrous DCM (1.25 L) was cooled to −78° C. To the solution was added 2.5M butyllithium solution (100 mL, 250 mmol in hexane) via cannula, maintaining the internal temperature below −68° C. The thick suspension was stirred for 20 minutes at −78° C. A solution of Intermediate 54 (24 g, 68.3 mmol) in anhydrous DCM (100 mL) was added, maintaining the internal temperature below −68° C. After addition, the mixture was stirred for 10 minutes, then saturated aqueous NH$_4$Cl solution (400 mL) and water (100 mL) were added. The mixture was allowed to warm to room temperature, then the organic phase was separated and the aqueous phase was extracted with DCM (2×300 mL). The combined organic phases were dried over Na$_2$SO$_4$, then filtered and evaporated in vacuo. The crude residue was purified by flash column chromatography (20-100% EtOAc in heptane), then recrystallized from heptane. The residue was further purified by flash column chromatography (20-35% EtOAc in heptane) to afford the title compound (0.93 g) as a white solid. $\delta_H$ (500 MHz, CDCl$_3$) 8.70 (s, 2H), 4.34 (s, 1H), 2.80-2.74 (m, 1H), 2.44-2.35 (m, 2H), 2.26-2.20 (m, 1H), 1.13 (s, 9H), 0.97 (s, 3H), 0.86-0.83 (m, 9H), 0.00 (s, 6H).

Intermediate 56

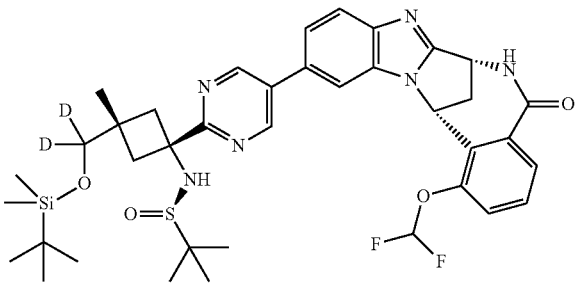 [SMILES: [2H]C([2H])(O[Si](C)(C)C(C)(C)C)[C@]1(C)C[C@@](N[S@](=O)C(C)(C)C)(c2ncc(-c3ccc4nc5n(c4c3)[C@@H]3C[C@H]5NC(=O)c4cccc(OC(F)F)c43)cn2)C1]

N-(cis-3-{[tert-Butyl(dimethyl)silyl]oxy(dideutero)methyl}-1-{5-[(7R,14R)-1-(difluoro-methoxy)-5-oxo-5,6,7,14-tetrahydro-7,14-methanobenzimidazo[1,2-b][2,5]-benzodiazocin-11-yl]pyrimidin-2-yl}-3-methylcyclobutyl)-2-methylpropane-2-sulfinamide A solution of Intermediate 55 (1.36 g, 2.51 mmol), (7R,14R)-1-(difluoro-methoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (WO 2016/050975, Intermediate 171) (1.32 g, 2.51 mmol) and potassium phosphate tribasic (2.13 g, 10 mmol) in 1,4 dioxane (5 mL) and water (1.5 mL) was degassed with nitrogen, then tris(dibenzylideneacetone)-dipalladium(0) (0.12 g, 0.13 mmol) and tricyclohexylphosphonium tetrafluoroborate (0.11 g, 0.3 mmol) were added. The reaction mixture was heated at 100° C. for 16 h, then diluted with water (5 mL) and extracted with EtOAc (3×15 mL). The organic phases were combined, washed with saturated brine (10 mL) and dried over Na$_2$SO$_4$, then filtered and evaporated in vacuo. The resulting brown oil was purified by column chromatography using a 55 g KP-NH column (50-100% EtOAc in heptane, followed by 0-15% MeOH in EtOAc) to give the title compound (1.68 g, 94%) as a yellow powder. 6H (500 MHz, DMSO-d$_6$) 9.15 (d, J6.8 Hz, 1H), 9.08 (s, 2H), 8.23 (dd, J7.7, 1.6 Hz, 1H), 7.84-7.67 (m, 3H), 7.64 (dd, J8.6, 1.7 Hz, 1H), 7.55-7.47 (m, 2H), 6.37 (d, J7.1 Hz, 1H), 5.64 (s, 1H), 4.90 (t, J 6.8 Hz, 1H), 3.54-3.45 (m, 1H), 2.75 (d, J13.3 Hz, 1H), 2.70 (d, J12.3 Hz, 1H), 2.46-2.40 (m, 3H), 1.07 (s, 9H), 0.94 (s, 3H), 0.89 (s, 9H), 0.07 (d, J 0.8 Hz, 6H). LCMS (ESI+) [M+H]+ 753.4, RT 1.87 minutes (Method 1).

Intermediate 57

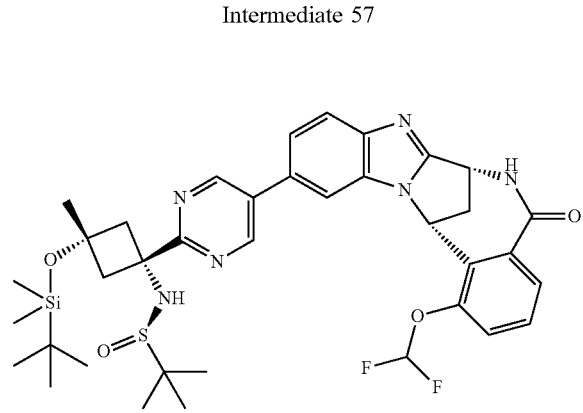

N-[cis-3-({[tert-Butyl(dimethyl)silyl]oxy}methyl)-1-{5-[(7R,14R)-1-(difluoromethoxy)-5-oxo-5,6,7,14-tetrahydro-7,14-methanobenzimidazo[1,2-b][2,5]benzodiazocin-11-yl]-pyrimidin-2-yl}-3-methylcyclobutyl]-2-methylpropane-2-sulfinamide Prepared from Intermediate 32 and (7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]-benzodiazocin-5(14H)-one (WO 2016/050975, Intermediate 171) following the experimental procedure described for Intermediate 56. LCMS (ESI+) [M+H]+ 751.2, RT 3.20 minutes (Method 1).

Intermediate 58

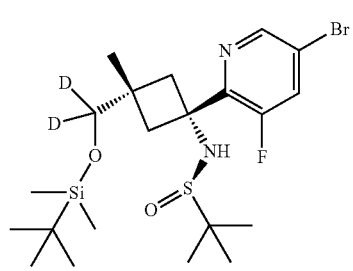 [SMILES: [2H]C([2H])(O[Si](C)(C)C(C)(C)C)[C@]1(C)C[C@@](N[S@](=O)C(C)(C)C)(c2ncc(Br)cc2F)C1]

N-[1-(5-Bromo-3-fluoropyridin-2-yl)-3-{[tert-butyl(dimethyl)silyl]oxy(dideuterio)-methyl}-3-methylcyclobutyl]-2-methylpropane-2-sulfinamide Prepared from Intermediate 54 and 2,5-dibromo-3-fluoropyridine following the experimental procedure described for Intermediate 55. δ_H (500 MHz, CDCl_3) 8.41-8.35 (m, 1H), 7.47 (dd, J9.9, 1.9 Hz, 1H), 3.76 (s, 1H), 2.70 (d, J12.9 Hz, 1H), 2.48-2.38 (m, 2H), 2.37-2.30 (m, 1H), 1.07 (s, 9H), 0.87 (s, 3H), 0.85 (s, 9H), 0.00 (s, 6H). LCMS (ESI+) [M+H]+ 509.05, RT 1.67 minutes (Method 1).

Intermediate 59

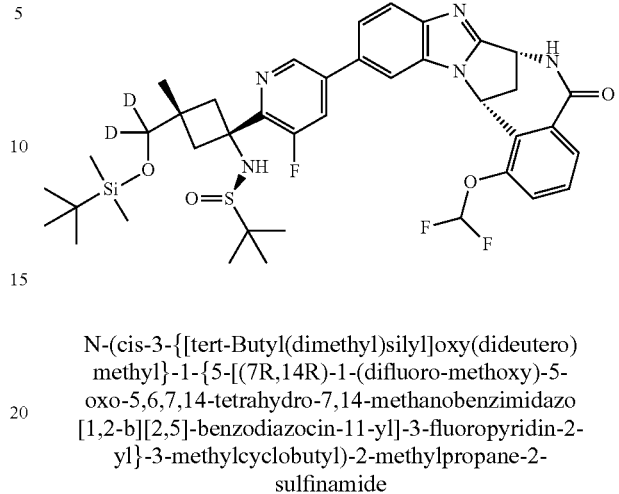

N-(cis-3-{[tert-Butyl(dimethyl)silyl]oxy(dideutero)methyl}-1-{5-[(7R,14R)-1-(difluoro-methoxy)-5-oxo-5,6,7,14-tetrahydro-7,14-methanobenzimidazo[1,2-b][2,5]-benzodiazocin-11-yl]-3-fluoropyridin-2-yl}-3-methylcyclobutyl)-2-methylpropane-2-sulfinamide Prepared from Intermediate 58 and (7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]-benzodiazocin-5(14H)-one (WO 2016/050975, Intermediate 171) following the experimental procedure described for Intermediate 56. δ_H (500 MHz, DMSO-d_6) 9.14 (d, J6.8 Hz, 1H), 8.73-8.62 (m, 1H), 8.23 (dd, J7.8, 1.5 Hz, 1H), 7.89 (dd, J12.2, 1.8 Hz, 1H), 7.86-7.54 (m, 4H), 7.54-7.47 (m, 2H), 6.36 (d, J7.1 Hz, 1H), 5.46 (s, 1H), 4.89 (t, J 6.8 Hz, 1H), 3.49 (dt, J13.4, 6.9 Hz, 1H), 2.74 (d, J13.3 Hz, 1H), 2.68-2.57 (m, 2H), 2.48-2.41 (m, 2H), 1.04 (s, 9H), 0.90 (s, 9H), 0.87 (s, 3H), 0.07 (d, J1.2 Hz, 6H). LCMS (ESI+) [M+H]+ 770.3, RT 1.60 minutes (Method 1).

Example 1

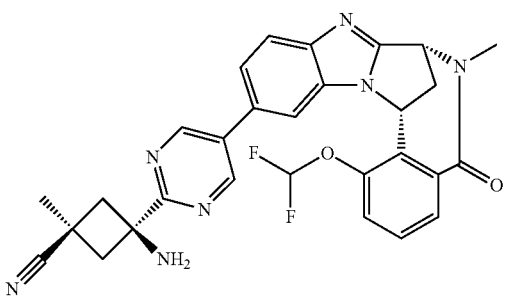 [SMILES: CN1C(=O)c2cccc(OC(F)F)c2[C@H]2C[C@@H]1c1nc3ccc(-c4cnc([C@]5(N)C[C@@](C)(C#N)C5)nc4)cc3n12]

cis-3-Amino-3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}-1-methyl-cyclobutanecarbonitrile To Intermediate 5 (178 mg, 0.24 mmol) dissolved in MeOH (5 mL) was added 4M hydrochloric acid in 1,4-dioxane (0.31 mL). The reaction mixture was stirred at r.t. for 90 minutes, then the solvent was removed in vacuo. The resulting brown glass was purified by flash column chromatography on silica (gradient elution with 100% DCM to 25% MeOH/DCM). The resulting mixture of cis and trans isomers was purified by preparative HPLC to afford the title compound (9 mg, 7%) as a white solid. δ$_H$ (300 MHz, DMSO-d$_6$) 9.07 (s, 2H), 8.32-8.20 (m, 1H), 7.96-7.40 (m, 6H), 6.31 (d, J7.1 Hz, 1H), 5.26 (d, J7.1 Hz, 1H), 3.52 (dt, J14.1, 7.4 Hz, 1H), 3.36 (s, 3H), 2.88-2.75 (m, 3H), 2.64-2.57 (m, 2H), 1.46 (s, 3H). LCMS (ES+) [M+H]$^+$ 542.0, RT 1.766 minutes (Method 1). LCMS (ES+) [M+H]$^+$ 542.2, RT 1.43 minutes (Method 2).

Example 2

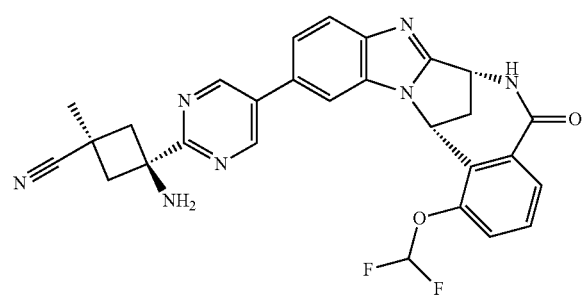 [SMILES: C[C@]1(C#N)C[C@](N)(c2ncc(-c3ccc4nc5n(c4c3)[C@@H]3C[C@H]5NC(=O)c4cccc(OC(F)F)c43)cn2)C1]

cis-3-Amino-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-1-methyl-cyclobutanecarbonitrile To Intermediate 6 (50 mg, 0.079 mmol) dissolved in 1,4-dioxane (5 mL) was added 4M hydrochloric acid in 1,4-dioxane (5 mL). The reaction mixture was stirred at r.t. for 1 h, then separated between EtOAc (10 mL) and 0.5M aqueous hydrochloric acid solution (10 mL). The aqueous layer was washed with DCM (2×10 mL), then basified with aqueous sodium carbonate solution and extracted into DCM. The organic layer was concentrated in vacuo. The resulting crude white solid (mixture of cis and trans isomers) was purified by preparative HPLC to afford the title compound (12 mg, 29%). δ$_H$ (300 MHz, DMSO-d$_6$) 9.15 (d, J 6.8 Hz, 1H), 9.07 (s, 2H), 8.23 (dd, J 5.7, 3.7 Hz, 1H), 7.97-7.43 (m, 6H), 6.36 (d, J6.9 Hz, 1H), 4.90 (t, J6.8 Hz, 1H), 3.59-3.39 (m, 1H), 2.85-2.68 (m, 3H), 2.65-2.57 (m, 2H), 1.46 (s, 3H). LCMS (ES+) [M+H]$^+$ 528.0, RT 1.69 minutes (Method 1).

Example 3

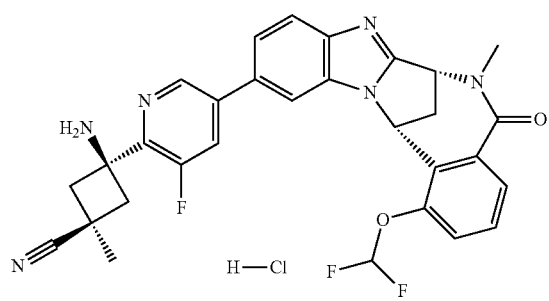

cis-3-Amino-3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-1-methylcyclobutanecarbonitrile Intermediate 8 (120 mg, 0.181 mmol) was dissolved in 4M hydrochloric acid in 1,4-dioxane (5 mL). The reaction mixture was stirred for 1 h. Diethyl ether was added, and the precipitate was filtered, to afford the title compound (82 mg, 81%) as a white solid (containing 7% of the trans isomer). δ$_H$ (300 MHz, DMSO-d$_6$) 8.99 (s, 3H), 8.84 (t, J 1.8 Hz, 1H), 8.28 (p, J 4.3 Hz, 1H), 8.20 (dd, J 12.3, 1.8 Hz, 1H), 7.95-7.43 (m, 6H), 6.31 (d, J 7.1 Hz, 1H), 5.28 (d, J 7.0 Hz, 1H), 3.61-3.49 (m, 1H), 3.36 (s, 3H), 3.33-3.13 (m, 4H), 2.86 (d, J 13.8 Hz, 1H), 1.29 (s, 3H). LCMS (ES+) [M+H]$^+$ 559.0, RT 1.93 minutes (Method 1). LCMS (ES+) [M+H]$^+$ 559.0, 1.71 minutes (Method 2).

Example 4

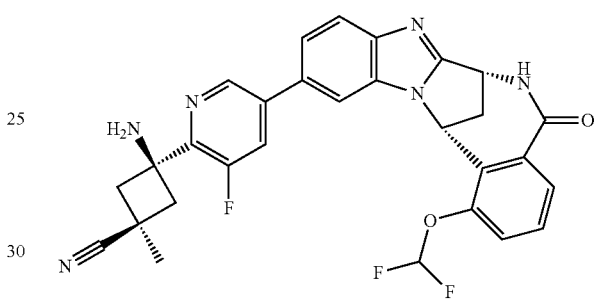

cis-3-Amino-3-{5-[(7R,14R)-1-(difluoromethoxy)-5-oxo-5,6,7,14-tetrahydro-7,14-methanobenzimidazo[1,2-b][2,5]benzodiazocin-11-yl]-3-fluoropyridin-2-yl}-1-methyl-cyclobutanecarbonitrile Intermediate 9 (102 mg, 0.157 mmol) was dissolved in 1,4-dioxane (5 mL) and treated with 4M hydrochloric acid in 1,4-dioxane (5 mL). The reaction mixture was stirred for 1 h. Diethyl ether was added, and the precipitate which formed was filtered. The crude residue (mixture of cis and trans isomers, 81 mg) was purified by preparative HPLC to afford the title compound (11 mg, 13%). δ$_H$ (300 MHz, DMSO-d$_6$) 9.15 (d, J 6.9 Hz, 1H), 8.62 (t, J 1.8 Hz, 1H), 8.23 (dd, J 6.4, 3.0 Hz, 1H), 7.99-7.44 (m, 7H), 6.35 (d, J 7.1 Hz, 1H), 4.89 (t, J 6.7 Hz, 1H), 3.49 (dt, J13.4, 7.2 Hz, 1H), 2.85-2.71 (m, 3H), 2.68-2.59 (m, 2H), 2.38 (s, 2H), 1.35 (s, 3H). LCMS (ES+) [M+H]$^+$ 545.0, RT 1.79 minutes (Method 1). LCMS (ES+) [M+H]$^+$ 545.2, RT 1.38 minutes (Method 2).

Example 5

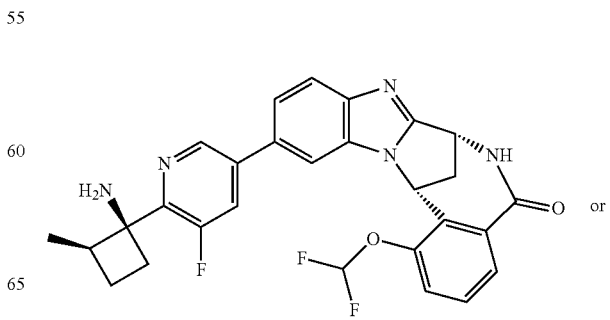

or

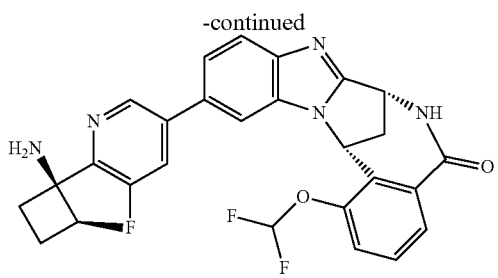

(7R,14R)-11-{6-[(1S,2R)-1-Amino-2-methylcyclobutyl]-5-fluoropyridin-3-yl}-1-(difluoromethoxy)-6,7-dihydro-7,14-methanobenzimidazo[1,2-b][2,5]benzodiazocin-5(14M)-one or (7R,14R)-11-{6-[(1R,2S)-1-Amino-2-methylcyclobutyl]-5-fluoropyridin-3-yl}-1-(difluoromethoxy)-6,7-dihydro-7,14-methanobenzimidazo[1,2-b][2,5]-benzodiazocin-5(14H)-one To Intermediate 12 (135 mg, 0.22 mmol) dissolved in acetonitrile (10 mL) was added 2M aqueous hydrochloric acid solution (10 mL). The reaction mixture was concentrated in vacuo and was treated with 2M aqueous sodium hydroxide solution (30 mL). The mixture was extracted with DCM (3×20 mL). The organic layers were combined and concentrated in vacuo. The crude residue was purified by flash column chromatography on silica (gradient elution with 0-20% MeOH in DCM) to afford the title compound (112 mg, 100%) as a white solid. $\delta_H$ (300 MHz, DMSO-$d_6$) 9.15 (d, J6.8 Hz, 1H), 8.60 (t, J1.9 Hz, 1H), 8.23 (dd, J 6.5, 3.0 Hz, 1H), 7.95-7.42 (m, 7H), 6.36 (d, J 7.1 Hz, 1H), 4.89 (t, J 6.8 Hz, 1H), 3.48 (dq, J13.9, 7.0 Hz, 1H), 2.83-2.67 (m, 2H), 2.61-2.52 (m, 1H), 2.01-1.82 (m, 4H), 1.80-1.63 (m, 1H), 1.14 (d, J6.8 Hz, 3H). LCMS (ES+) [M+H]$^+$ 520.0, RT 1.68 minutes (Method 1). LCMS (ES+) [M+H]$^+$ 520.2, RT 1.45 minutes (Method 2).

Example 6

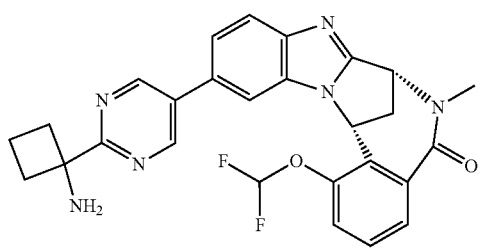 [SMILES: CN1C(=O)c2cccc(OC(F)F)c2[C@H]2C[C@@H]1c1nc3ccc(-c4cnc(C5(N)CCC5)nc4)cc3n12]

(7R,14R)-11-[2-(1-Aminocyclobutyl)pyrimidin-5-yl]-1-(difluoromethoxy)-6-methyl-6,7-dihydro-7,14-methanobenzimidazo[1,2-b][2,5]benzodiazocin-5(14H)-one To a solution of Intermediate 17 (18.0 g, 29.9 mmol) in 1,4-dioxane (25 mL) was added 4M hydrochloric acid in 1,4-dioxane (40 mL). The resulting mixture was stirred at room temperature for 1 h, then concentrated in vacuo. The residue was dissolved in water (500 mL) and washed with EtOAc (2×300 mL). The aqueous layer was basified to pH 9 with 2N aqueous sodium hydroxide solution, which resulted in precipitation of a solid. EtOAc (500 mL) was added and the mixture was stirred until all solids had dissolved. The residue was partitioned, then the aqueous layer was further extracted with EtOAc (500 mL). The combined organic layers were dried over Na$_2$SO$_4$ and filtered, then concentrated in vacuo and dried overnight under high vacuum. The foamy residue was suspended in a mixture of diethyl ether and hexane (150 mL), then stirred and shaken vigorously, before being concentrated in vacuo, to afford the title compound (12.4 g, 83%) as a white amorphous solid. $\delta_H$ (400 MHz, DMSO-$d_6$) 9.05 (s, 2H), 8.32-8.22 (m, 1H), 7.91-7.66 (m, 3H), 7.62 (dd, J8.5, 1.8 Hz, 1H), 7.53-7.46 (m, 2H), 6.31 (d, J7.1 Hz, 1H), 5.26 (d, J 7.2 Hz, 1H), 3.52 (dt, J 14.2, 7.3 Hz, 1H), 3.36 (s, 3H), 2.84 (d, J 13.8 Hz, 1H), 2.63 (dtd, J11.5, 5.6, 2.5 Hz, 2H), 2.38 (s, 2H), 2.16-2.05 (m, 2H), 2.04-1.91 (m, 1H), 1.87-1.73 (m, 1H). LCMS (ES+APCI) [M-NH$_2$]$^-$ 486.0, RT 1.66 minutes (Method 2). LCMS (ES+) [M+H]$^+$ 503.0, RT 1.71 minutes (Method 1).

Example 7

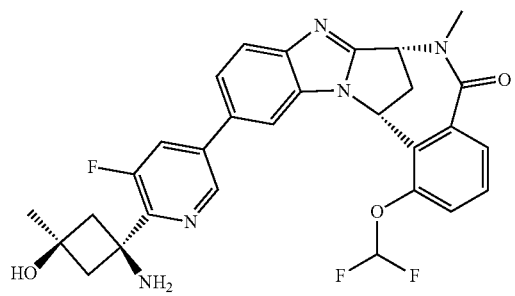 [SMILES: CN1C(=O)c2cccc(OC(F)F)c2[C@H]2C[C@@H]1c1nc3ccc(-c4cnc([C@]5(N)C[C@@](C)(O)C5)c(F)c4)cc3n12]

(7R,14R)-11-[6-(cis-1-Amino-3-hydroxy-3-methylcyclobutyl)-5-fluoropyridin-3-yl]-1-(difluoromethoxy)-6-methyl-6,7-dihydro-7,14-methanobenzimidazo[1,2-b][2,5]-benzodiazocin-5(14H)-one Hydrochloric acid in 1,4-dioxane (4.0M, 100 mL, 400 mmol) was added to a stirred solution of Intermediate 24 (44.6 g, 58.1 mmol) in MeOH (290 mL). The reaction mixture was stirred at r.t. for 3 h, then diluted with DCM (400 mL). Water (400 mL) was added, then the layers were separated. The organic layer was extracted with 2N aqueous hydrochloric acid solution (2×200 mL). The combined aqueous extracts were washed twice with DCM. The aqueous layer was rendered alkaline with solid potassium carbonate, and extra water was added. The aqueous suspension was extracted three times with DCM/MeOH mixture (~1:1). The combined organic extracts were dried (Na$_2$SO$_4$), filtered and concentrated in vacuo. The crude residue was triturated with diethyl ether and the mixture was stirred for 60 h. The beige solids were collected by filtration, then washed with diethyl ether and dried over a stream of air, to afford the title compound (26.5 g, 83%). $\delta_H$ (400 MHz, DMSO-$d_6$) 8.62 (s, 1H), 8.31-8.23 (m, 1H), 7.92-7.86 (m, 1H), 7.77-7.72 (m, 2H), 7.70 (t, J 71.9 Hz, 1H), 7.60 (d, J 9.3 Hz, 1H), 7.52-7.48 (m, 2H), 6.30 (d, J7.1 Hz, 1H), 5.25 (d, J7.1 Hz, 1H), 5.01 (s, 1H), 3.56-3.47 (m, 1H), 3.36 (s, 3H), 2.86 (t, J 13.3 Hz, 3H), 2.26-2.18 (m, 4H), 1.00 (s, 3H). LCMS [M+H]$^+$ 550, RT 2.37 minutes (Method 7).

Example 8

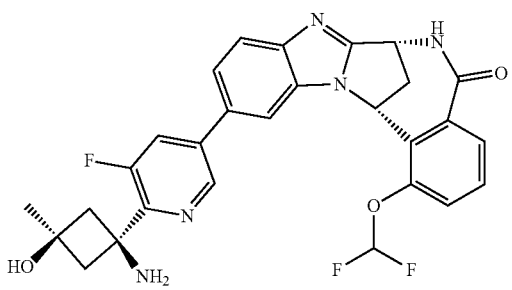 [SMILES: C[C@]1(O)C[C@](N)(c2ncc(-c3ccc4nc5n(c4c3)[C@@H]3C[C@H]5NC(=O)c4cccc(OC(F)F)c43)cc2F)C1]

(7R,14R)-11-[6-(cis-1-Amino-3-hydroxy-3-methyl-cyclobutyl)-5-fluoropyridin-3-yl]-1-(difluoromethoxy)-6,7-dihydro-7,14-methanobenzimidazo[1,2-b][2,5]benzodiazocin-5(14H)-one Intermediate 25 (930 mg, 1.23 mmol) was dissolved in ethanol (20 mL) and 4M hydrochloric acid in 1,4-dioxane (5 mL) was added at 0° C. The reaction mixture was warmed to r.t. and stirred overnight, then concentrated in vacuo. The residue was re-dissolved in aqueous 1M hydrochloric acid and washed twice with DCM. The aqueous layer was basified to pH 10 with 2M aqueous sodium hydroxide solution and extracted with three portions of DCM. The organic phases were combined and concentrated in vacuo. The crude residue was purified by flash column chromatography on silica (gradient elution with 0-100% EtOAc/hexane, followed by 0-20% MeOH/[10% 7N ammonia in MeOH/DCM]) to afford the title compound (580 mg, 88%). $\delta_H$ (300 MHz, DMSO-$d_6$) 9.15 (d, J 6.8 Hz, 1H), 8.62 (d, J 2.3 Hz, 1H), 8.23 (dd, J 6.7, 2.8 Hz, 1H), 7.98-7.80 (m, 1H), 7.79-7.65 (m, 3H), 7.64-7.38 (m, 3H), 6.36 (d, J 7.0 Hz, 1H), 5.00 (s, 1H), 4.89 (t, J 6.7 Hz, 1H), 3.49 (dt, J 13.4, 7.1 Hz, 1H), 2.87 (d, J 11.7 Hz, 2H), 2.75 (d, J 13.3 Hz, 1H), 2.22 (t, J 6.0 Hz, 4H), 1.00 (s, 3H). LCMS (ES+) [M+H]$^+$ 536.0, RT 1.52 minutes (Method 1). LCMS (ES+) [M+H]$^+$ 536.2, RT 1.26 minutes (Method 2).

Example 9

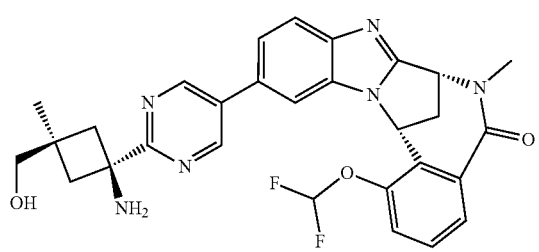 [SMILES: CN1C(=O)c2cccc(OC(F)F)c2[C@H]2C[C@@H]1c1nc3ccc(-c4cnc([C@]5(N)C[C@@](C)(CO)C5)nc4)cc3n12]

(7R,14R)-11-{2-[cis-1-Amino-3-(hydroxymethyl)-3-methylcyclobutyl]pyrimidin-5-yl}-1-(difluoromethoxy)-6-methyl-6,7-dihydro-7,14-methanobenzimidazo[1,2-b][2,5]-benzodiazocin-5(14H)-one Hydrochloric acid in 1,4-dioxane (4.0M, 34.3 mL, 137 mmol) was added to a stirred solution of Intermediate 33 (17.5 g, 22.9 mmol) in MeOH (114 mL). The reaction mixture was stirred at r.t. for 2 h, then DCM (200 mL) and water (200 mL) were added. The layers were separated and the organic layer was extracted with aqueous 2N hydrochloric acid solution (2×100 mL). The combined aqueous phases were washed with DCM (2×100 mL), then rendered alkaline with solid potassium carbonate. The aqueous suspension was extracted with DCM/MeOH mixture (~1:1; 4×150 mL). The combined organic extracts were dried (Na$_2$SO$_4$), filtered and concentrated in vacuo. The crude residue was triturated with diethyl ether and stirred overnight. The suspension was filtered and air dried to afford the title compound (11.3 g, 90%) as a pale beige solid. $\delta_H$ (400 MHz, DMSO-$d_6$) 9.06 (s, 2H), 8.30-8.25 (m, 1H), 7.78 (d, J8.5 Hz, 1H), 7.75 (s, 1H), 7.69 (t, J73.3 Hz, 1H), 7.63 (d, J8.5 Hz, 1H), 7.50 (d, J5.7 Hz, 2H), 6.31 (d, J7.1 Hz, 1H), 5.26 (d, J7.1 Hz, 1H), 3.57-3.48 (m, 1H), 3.45 (s, 2H), 3.36 (s, 3H), 2.84 (d, J 13.8 Hz, 1H), 2.46 (d, J12.6 Hz, 2H), 2.09 (d, J12.8 Hz, 2H), 1.07 (s, 3H). LCMS [M+H]$^+$ 547, RT 2.45 minutes (Method 7).

Example 10

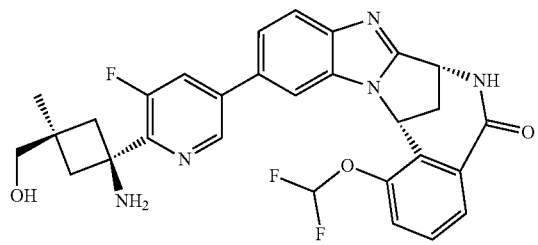 [SMILES: C[C@]1(CO)C[C@](N)(c2ncc(-c3ccc4nc5n(c4c3)[C@@H]3C[C@H]5NC(=O)c4cccc(OC(F)F)c43)cc2F)C1]

(7R,14R)-11-{6-[cis-1-Amino-3-(hydroxymethyl)-3-methylcyclobutyl]-5-fluoropyridin-3-yl}-1-(difluoromethoxy)-6,7-dihydro-7,14-methanobenzimidazo[1,2-b][2,5]-benzodiazocin-5(14H)-one Intermediate 35 (347 mg, 0.45 mmol) was dissolved in ethanol (10 mL) and 4M hydrochloric acid in 1,4-dioxane (2.5 mL) was added at 0° C. The reaction mixture was warmed to r.t. and stirred overnight. The reaction mixture was concentrated in vacuo, re-dissolved in 1M aqueous hydrochloric acid and washed twice with DCM. The aqueous layer was basified to pH 10 with 2M aqueous sodium hydroxide solution and extracted with three portions of DCM. The organic phases were combined and concentrated in vacuo. The crude residue was purified on silica (gradient elution with 0-100% EtOAc/hexane, then 0-50% DCM/[10% 7N ammonia in MeOH]) to afford the title compound (194 mg, 78%). $\delta_H$(300 MHz, DMSO-$d_6$) 9.15 (d, J6.8 Hz, 1H), 8.62 (t, J 1.8 Hz, 1H), 8.23 (dd, J 6.5, 2.8 Hz, 1H), 7.96-7.39 (m, 7H), 6.36 (d, J 7.1 Hz, 1H), 4.89 (t, J 6.8 Hz, 1H), 3.57-3.45 (m, 1H), 3.43 (s, 2H), 2.75 (d, J 13.2 Hz, 1H), 2.49-2.43 (m, 2H), 2.14 (d, J 12.6 Hz, 2H), 0.94 (s, 3H). LCMS (ES+) [M+H]$^+$ 550.0, RT 1.68 minutes (Method 1). LCMS (ES+) [M+H]$^+$ 550.2, RT 1.46 minutes (Method 2).

Example 11

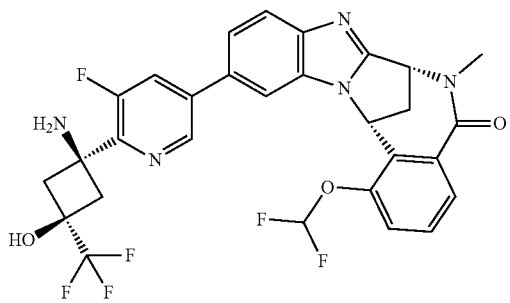 [SMILES: CN1C(=O)c2cccc(OC(F)F)c2[C@H]2C[C@@H]1c1nc3ccc(-c4cnc([C@]5(N)C[C@](O)(C(F)(F)F)C5)c(F)c4)cc3n12]

(7R,14R)-11-{6-[cis-1-Amino-3-hydroxy-3-(trifluoromethyl)cyclobutyl]-5-fluoropyridin-3-yl}-1-(difluoromethoxy)-6-methyl-6,7-dihydro-7,14-methanobenzimidazo[1,2-b][2,5]-benzodiazocin-5(14H)-one Hydrogen chloride in 1,4-dioxane (4M, 8.72 mL) was added to a stirred solution of Intermediate 43 (823 mg, 1.16 mmol) in 1,4-dioxane (15 mL) at r.t. The mixture was stirred for 0.5 h, then concentrated in vacuo. The resulting off-white solid was dissolved in MeOH (10 mL) and loaded onto an ion-exchange cartridge (SCX-2), which was washed with MeOH (2×15 mL). The material was eluted with 2.0M ammonia in MeOH (3×15 mL). The filtrate was concentrated in vacuo. Flash column chromatography of the crude residue (mixture of trans and cis isomers, 642 mg) on reverse phase silica (gradient elution with 10-23% acetonitrile in water spiked with 0.1% formic acid) afforded the first eluting fraction (trans isomer, 295 mg) as an opaque gum, which was suspended in 1:1 acetonitrile-water (4 mL) and treated with 1M aqueous hydrochloric acid solution (538 µL). The resulting solution was freeze-dried to afford the trans isomer (298 mg, 42%) as a colourless solid. The second eluting fraction (cis isomer) was concentrated in vacuo and re-purified via preparative HPLC (eluting with 0-100% acetonitrile in water spiked with 0.1% formic acid). The resulting off-white solid (mono-formate salt) was dissolved in MeOH (15 mL) and loaded onto an ion-exchange column (SCX-2). The material was washed with MeOH (2×15 mL) and eluted with 2.0M ammonia in MeOH (3×15 mL). The filtrate was concentrated in vacuo. The resulting opaque glass (free base, 147 mg) was suspended in 1:1 acetonitrile-water (4 mL) and treated with 1M aqueous hydrochloric acid solution (268 µL). The resulting solution was freeze-dried to afford the title compound (cis isomer, 144 mg, 21%) as a colourless solid. $\delta_H$ (500 MHz, CD$_3$OD) 8.84 (d, J 1.5 Hz, 1H), 8.46-8.39 (m, 1H), 8.07 (dd, J12.1, 1.8 Hz, 1H), 8.04 (d, J1.3 Hz, 1H), 7.90 (d, J8.6 Hz, 1H), 7.83 (dd, J8.6, 1.6 Hz, 1H), 7.57-7.52 (m, 2H), 7.51-7.21 (m, 1H), 6.64 (d, J 7.2 Hz, 1H), 5.48 (d, J 7.2 Hz, 1H), 3.75-3.65 (m, 1H), 3.58 (d, J 15.1 Hz, 2H), 3.51 (s, 3H), 3.05 (d, J 13.9 Hz, 1H), 2.76 (d, J 15.3 Hz, 2H). LCMS (ESI) [M+H]$^+$ 604.2, RT 2.04 minutes (Method 11).

Example 12

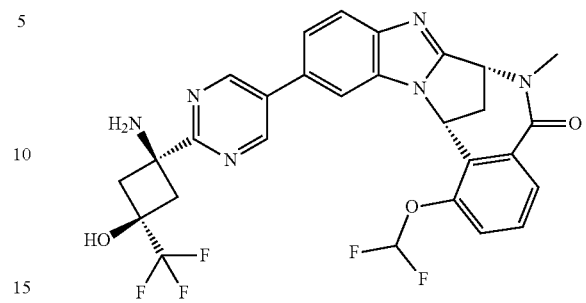

(7R,14R)-11-{2-[c is-1-Amino-3-hydroxy-3-(trifluoromethyl)cyclobutyl]pyrimidin-5-yl}-1-(difluoromethoxy)-6-methyl-6,7-dihydro-7,14-methanobenzimidazo[1,2-b][2,5]-benzodiazocin-5(14H)-one Hydrogen chloride in 1,4-dioxane (4M, 5.15 mL) was added to a stirred solution of Intermediate 46 (474 mg, 0.69 mmol) in 1,4-dioxane (10 mL) at ambient temperature. The mixture was stirred for 2 h, then concentrated in vacuo. The resulting crude off-white solid was dissolved in MeOH (10 mL) and loaded onto an ion exchange column (SCX-2), which was washed with MeOH (2×25 mL). The material was eluted with 2.0M ammonia in MeOH (3×15 mL). The filtrate was concentrated in vacuo. Purification of the crude residue (mixture of trans and cis isomers, 396 mg) by preparative HPLC (eluting with 0-100% formic acid in acetonitrile) afforded the first eluting fraction (trans isomer), which was concentrated in vacuo, then dissolved in MeOH (5 mL) and loaded onto an ion-exchange column (SCX-2). The column was washed with MeOH (2×15 mL) and the material was eluted with 2.0M ammonia in MeOH (3×15 mL). The filtrate was concentrated in vacuo. The resulting opaque glass (free base, 215 mg) was suspended in 1:1 acetonitrile-water (4 mL) and treated with 1M aqueous hydrochloric acid solution (400 µL). The resulting solution was freeze-dried to give the trans isomer (203 mg, 47%) as a colourless solid. The second eluting fraction (cis isomer) was concentrated in vacuo, then dissolved in MeOH (5 mL) and loaded onto an ion exchange column (SCX-2). The column was washed with MeOH (2×15 mL) and the material was eluted with 2.0M ammonia in MeOH (3×15 mL). The filtrate was concentrated in vacuo. The resulting opaque glass (free base, 118 mg) was suspended in 1:1 acetonitrile-water (2 mL) and treated with 1M aqueous hydrochloric acid solution (222 µL). The resulting solution was freeze-dried to give the title compound (cis isomer, 118 mg, 24%) as a colourless solid. $\delta_H$ (500 MHz, CD$_3$OD) 9.19 (s, 2H), 8.44-8.36 (m, 1H), 8.00 (d, J 1.2 Hz, 1H), 7.89 (d, J 8.6 Hz, 1H), 7.81-7.72 (m, 1H), 7.54-7.49 (m, 2H), 7.49-7.21 (m, 1H), 6.59 (d, J 7.1 Hz, 1H), 5.42 (d, J 7.2 Hz, 1H), 3.72-3.64 (m, 1H), 3.58-3.53 (m, 2H), 3.51 (s, 3H), 3.01 (d, J 13.9 Hz, 1H), 2.67-2.59 (m, 2H). LCMS (ESI) [M+H]$^+$ 587.2, RT 1.95 minutes (Method 11).

Example 13

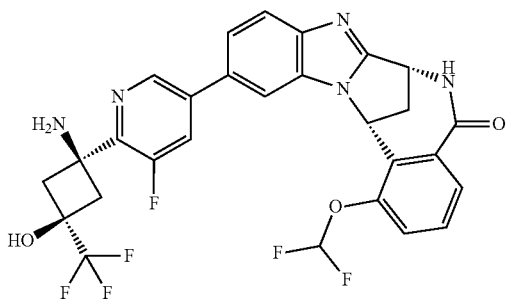 [SMILES: N[C@]1(c2ncc(-c3ccc4nc5n(c4c3)[C@@H]3C[C@H]5NC(=O)c4cccc(OC(F)F)c43)cc2F)C[C@@](O)(C(F)(F)F)C1]

(7R,14R)-11-{6-[cis-1-Amino-3-hydroxy-3-(trifluoromethyl)cyclobutyl]-5-fluoropyridin-3-yl}-1-(difluoromethoxy)-6,7-dihydro-7,14-methanobenzimidazo[1,2-b][2,5]-benzodiazocin-5(14H)-one To a solution of Intermediate 48 (440 mg, 0.55 mmol) in 1,4-dioxane (8 mL) was added 4M hydrogen chloride in 1,4-dioxane (4.14 mL). The reaction mixture was stirred at r.t. for 1 h, then concentrated in vacuo. The crude residue was loaded onto an ion-exchange column (SCX-2) in DCM/MeOH. The column was washed with MeOH (50 mL), and the product was eluted with 2M ammonia in MeOH (50 mL). The crude material (mixture of trans and cis isomers, 350 mg) was purified by preparative HPLC. The fraction containing cis isomer was suspended in 1:1 acetonitrile-water (4 mL) and treated with 4M hydrogen chloride in 1,4-dioxane (300 μL). The solution was freeze-dried to afford the title compound (hydrochloride salt, 132 mg, 38%) as an off-white powder. $\delta_H$ (500 MHz, CD$_3$OD) 8.82 (t, J 1.6 Hz, 1H), 8.36 (dd, J 7.2, 2.2 Hz, 1H), 8.04 (dd, J 12.2, 1.8 Hz, 1H), 7.95 (d, J 1.3 Hz, 1H), 7.82 (d, J 8.5 Hz, 1H), 7.70 (dd, J 8.6, 1.7 Hz, 1H), 7.58-7.17 (m, 3H), 6.60 (d, J7.1 Hz, 1H), 5.15-5.05 (m, 1H), 3.66-3.53 (m, 3H), 2.93 (d, J 13.5 Hz, 1H), 2.79-2.71 (m, 2H). LCMS (ESI) [M+H]$^+$ 590.1, RT 1.65 minutes (Method 11).

Example 14

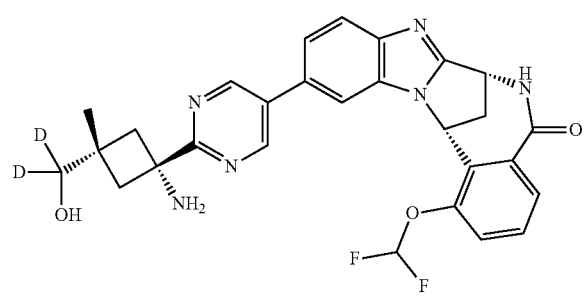 [SMILES: [2H]C([2H])(O)[C@]1(C)C[C@@](N)(c2ncc(-c3ccc4nc5n(c4c3)[C@@H]3C[C@H]5NC(=O)c4cccc(OC(F)F)c43)cn2)C1]

(7R,14R)-11-(2-{cis-1-Amino-3-[hydroxy(dideutero)methyl]-3-methylcyclobutyl}-pyrimidin-5-yl)-1-(difluoromethoxy)-6,7-dihydro-7,14-methanobenzimidazo[1,2-b][2,5]-benzodiazocin-5(14H)-one To a stirred solution of Intermediate 56 (500 mg, 0.66 mmol) in 1,4-dioxane (5 mL) was added 4M hydrogen chloride in 1,4-dioxane (0.66 mL). The reaction mixture was stirred at r.t. for 18 h, then concentrated under reduced pressure. The resulting off-white solid was purified using a 20 g SCX-2 cartridge (eluting with 2M ammonia in methanol). The resulting off-white solid was further purified by reverse-phase column chromatography (10-60% acetonitrile in water (+0.1% formic acid)). The relevant fractions were combined and the solvent was removed under reduced pressure. The resulting colourless gum was suspended in 1:1 acetonitrile:water and 1M HCl (1.3 equivalents) was added. The resulting solution was freeze-dried to afford the title compound, hydrochloride salt (199 mg) as a white powder. $\delta_H$ (500 MHz, DMSO-d$_6$) 9.22 (s, 2H), 9.19 (d, J6.9 Hz, 1H), 8.77 (s, 3H), 8.26-8.20 (m, 1H), 7.87-7.54 (m, 4H), 7.55-7.49 (m, 2H), 6.40 (d, J7.1 Hz, 1H), 4.96 (t, J6.9 Hz, 1H), 3.54-3.48 (m, 1H), 2.78 (d, J13.3 Hz, 1H), 2.62 (d, J14.0 Hz, 2H), 2.53-2.51 (m, 2H), 1.21 (s, 3H). LCMS (ESI+) [M+H]$^+$ 535.3, RT 2.25 minutes (Method 1).

Example 15

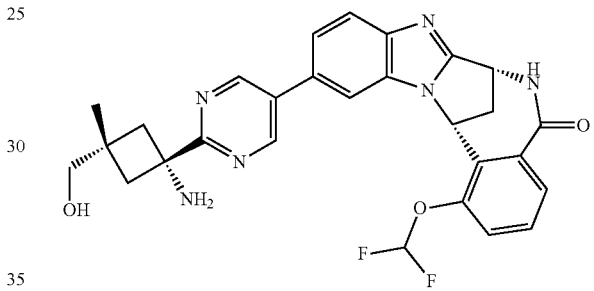

(7R,14R)-11-{2-[cis-1-Amino-3-(hydroxymethyl)-3-methylcyclobutyl]pyrimidin-5-yl}-1-(difluoromethoxy)-6,7-dihydro-7,14-methanobenzimidazo[1,2-b][2,5]benzodiazocin-5(14H)-one To a solution of Intermediate 57 (180 mg, 0.24 mmol) in ethanol (12 mL) at 0° C. was added 4M hydrochloric acid in 1,4-dioxane (2.5 mL, 10 mmol). The reaction mixture was warmed to r.t. and stirred overnight, then concentrated in vacuo. The residue was re-dissolved in 1M aqueous HCl solution and washed with DCM (2×2.5 mL). The aqueous layer was basified to pH 10 with 2M aqueous NaOH solution and extracted with DCM (2×2.5 mL). The organic phases were combined and concentrated in vacuo. The crude residue was purified by column chromatography (0-100% EtOAc in hexane, followed by 0-20% MeOH and 10% 7N ammonia in DCM) to give the title compound (62 mg, 49%) as a white solid. $\delta_H$ (300 MHz, DMSO-d$_6$) 9.15 (d, J6.8 Hz, 1H), 9.05 (s, 2H), 8.23 (dd, J 5.9, 3.6 Hz, 1H), 7.81-7.66 (m, 2H), 7.77 (t, J 48 Hz, 1H), 7.61 (dd, J8.5, 1.8 Hz, 1H), 7.55-7.41 (m, 2H), 6.37 (d, J 7.1 Hz, 1H), 5.50 (br s, 1H), 4.90 (t, J 6.7 Hz, 1H), 3.50 (dd, J 13.6, 6.9 Hz, 1H), 3.45 (s, 2H), 2.75 (d, J 13.5 Hz, 1H), 2.44 (d, J 12.9 Hz, 2H), 2.09 (d, J 12.9 Hz, 2H), 1.07 (s, 3H). LCMS (ESI+) [M+H]$^+$ 533, RT 1.51 minutes (Method 1).

Example 16

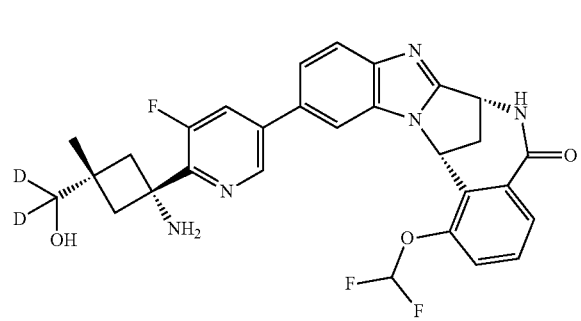 [SMILES: [2H]C([2H])(O)[C@]1(C)C[C@@](N)(c2ncc(-c3ccc4nc5n(c4c3)[C@@H]3C[C@H]5NC(=O)c4cccc(OC(F)F)c43)cc2F)C1]

(7R,14R)-11-(6-{cis-1-Amino-3-[hydroxy(dideutero)methyl]-3-methylcyclobutyl}-5-fluoropyridin-3-yl)-1-(difluoromethoxy)-6,7-dihydro-7,14-methanobenzimidazo[1,2-b]-[2,5]benzodiazocin-5(14H)-one Intermediate 59 (130 mg, 0.17 mmol) was dissolved in 1,4-dioxane (3 mL) and 4M hydrochloric acid in 1,4-dioxane (0.9 mL) was added. The mixture was stirred for 10 minutes, then diluted with methanol (3 mL) and stirred for 2 h. The mixture was concentrated in vacuo and the residue was purified on a 10 g SCX cartridge (eluting with 2M ammonia in methanol). The residue was dissolved in 1:1 acetonitrile:water (~5 mL), then treated with aqueous HCl (1.2 equivalents) and freeze-dried, to afford the title compound, hydrochloride salt (80 mg, 79%) as an off-white solid. $\delta_H$ (500 MHz, DMSO-$d_6$) 9.16 (d, J 6.9 Hz, 1H), 8.85-8.77 (m, 1H), 8.67 (s, 3H), 8.24 (dd, J 6.3, 3.1 Hz, 1H), 8.15 (dd, J12.7, 1.8 Hz, 1H), 7.87-7.54 (m, 4H), 7.54-7.48 (m, 2H), 6.37 (d, J 7.1 Hz, 1H), 4.93 (t, J6.8 Hz, 1H), 3.53-3.48 (m, 1H), 2.77 (d, J 13.3 Hz, 1H), 2.75-2.69 (m, 2H), 2.57 (d, J 13.5 Hz, 2H), 1.08 (s, 3H). LCMS (ESI+) [M+H]$^+$ 552.5, RT 1.99 minutes (Method 1).

The invention claimed is:

1. A compound of formula (I), or a pharmaceutically acceptable salt thereof:

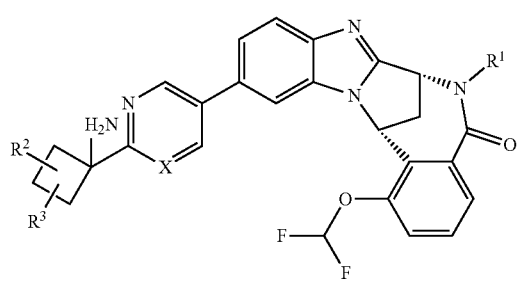

(I)

wherein
X represents N or C-F;
$R^1$ represents hydrogen or methyl;
$R^2$ represents hydrogen, methyl or trifluoromethyl; and
$R^3$ represents hydrogen, cyano, or hydroxymethyl.

2. The compound as claimed in claim 1 represented by formula (IIA), or a pharmaceutically acceptable salt thereof:

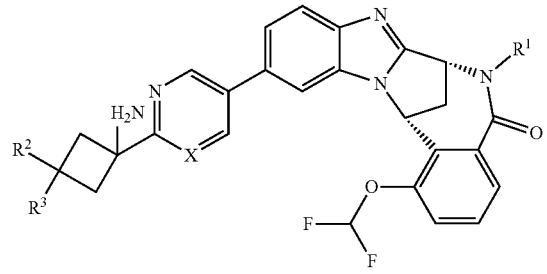

(IIA)

wherein X, $R^1$, $R^2$ and $R^3$ are as defined in claim 1.

3. The compound as claimed in claim 1 represented by formula (IIB), or a pharmaceutically acceptable salt thereof:

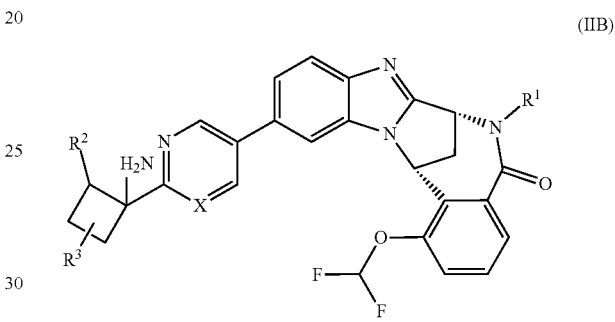

(IIB)

wherein X, $R^1$, $R^2$ and $R^3$ are as defined in claim 1.

4. A compound selected from the following:
cis-3-amino-3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}-1-methyl-cyclobutanecarbonitrile;
cis-3-amino-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-1-methyl-cyclobutanecarbonitrile;
cis-3-amino-3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]-3-fluoropyridin-2-yl}-1-methylcyclobutanecarbonitrile;
cis-3-amino-3-{5-[(7R,14R)-1-(difluoromethoxy)-5-oxo-5,6,7,14-tetrahydro-7,14-methanobenzimidazo[1,2-b][2,5]benzodiazocin-11-yl]-3-fluoropyridin-2-yl}-1-methylcyclobutanecarbonitrile;
(7R,14R)-11-{6-[(1S,2R)-1-amino-2-methylcyclobutyl]-5-fluoropyridin-3-yl}-1-(difluoromethoxy)-6,7-dihydro-7,14-methanobenzimidazo[1,2-b][2,5]benzodiazocin-5(14H)-one;
(7R,14R)-11-{6-[(1R,2S)-1-amino-2-methylcyclobutyl]-5-fluoropyridin-3-yl}-1-(difluoromethoxy)-6,7-dihydro-7,14-methanobenzimidazo[1,2-b][2,5]-benzodiazocin-5(14H)-one;
(7R,14R)-11-[2-(1-aminocyclobutyl)pyrimidin-5-yl]-1-(difluoromethoxy)-6-methyl-6,7-dihydro-7,14-methanobenzimidazo[1,2-b][2,5]benzodiazocin-5(14H)-one;
(7R,14R)-11-[6-(cis-1-amino-3-hydroxy-3-methylcyclobutyl)-5-fluoropyridin-3-yl]-1-(difluoromethoxy)-6-methyl-6,7-dihydro-7,14-methanobenzimidazo[1,2-b][2,5]-benzodiazocin-5(14H)-one;

(7R,14R)-11-[6-(cis-1-amino-3-hydroxy-3-methylcyclobutyl)-5-fluoropyridin-3-yl]-1-(difluoromethoxy)-6,7-dihydro-7,14-methanobenzimidazo[1,2-b][2,5]benzodiazocin-5(14H)-one;

(7R,14R)-11-{2-[cis-1-amino-3-(hydroxymethyl)-3-methylcyclobutyl]pyrimidin-5-yl}-1-(difluoromethoxy)-6-methyl-6,7-dihydro-7,14-methanobenzimidazo[1,2-b][2,5]-benzodiazocin-5(14H)-one;

(7R,14R)-11-(6-[cis-1-amino-3-(hydroxymethyl)-3-methylcyclobutyl]-5-fluoropyridin-3-yl}-1-(difluoromethoxy)-6,7-dihydro-7,14-methanobenzimidazo[1,2-b][2,5]-benzodiazocin-5(14H)-one;

(7R,14R)-11-(6-[cis-1-amino-3-hydroxy-3-(trifluoromethyl)cyclobutyl]-5-fluoropyridin-3-yl}-1-(difluoromethoxy)-6-methyl-6,7-dihydro-7,14-methanobenzimidazo[1,2-b][2,5]-benzodiazocin-5(14H)-one;

(7R,14R)-11-{2-[cis-1-amino-3-hydroxy-3-(trifluoromethyl)cyclobutyl]pyrimidin-5-yl}-1-(difluoromethoxy)-6-methyl-6,7-dihydro-7,14-methanobenzimidazo[1,2-b][2,5]-benzodiazocin-5(14H)-one;

(7R,14R)-11-(6-[cis-1-amino-3-hydroxy-3-(trifluoromethyl)cyclobutyl]-5-fluoropyridin-3-yl}-1-(difluoromethoxy)-6,7-dihydro-7,14-methanobenzimidazo[1,2-b][2,5]-benzodiazocin-5(14H)-one;

(7R,14R)-11-(2-{cis-1-amino-3-[hydroxy(dideutero)methyl]-3-methylcyclobutyl}-pyrimidin-5-yl)-1-(difluoromethoxy)-6,7-dihydro-7,14-methanobenzimidazo[1,2-b][2,5]-benzodiazocin-5(14H)-one;

(7R,14R)-11-{2-[cis-1-amino-3-(hydroxymethyl)-3-methylcyclobutyl]pyrimidin-5-yl}-1-(difluoromethoxy)-6,7-dihydro-7,14-methanobenzimidazo[1,2-b][2,5]benzodiazocin-5(14H)-one; and (7R,14R)-11-(6-{cis-1-amino-3-[hydroxy(dideutero)methyl]-3-methylcyclobutyl}-5-fluoropyridin-3-yl)-1-(difluoromethoxy)-6,7-dihydro-7,14-methanobenzimidazo[1,2-b]-[2,5]benzodiazocin-5(14H)-one.

5. A pharmaceutical composition comprising a compound of formula (I) as defined in claim 1, or a pharmaceutically acceptable salt thereof, in association with a pharmaceutically acceptable carrier.

6. A pharmaceutical composition comprising a compound of formula (I) as defined in claim 4, or a pharmaceutically acceptable salt thereof, in association with a pharmaceutically acceptable carrier.

\* \* \* \* \*